United States Patent
Kolan et al.

(10) Patent No.: US 11,925,394 B1
(45) Date of Patent: Mar. 12, 2024

(54) METHODS FOR CREATING, INSERTING, AND REMOVING AN INTRAMEDULLARY SLEEVE SYSTEM FOR BONE TREATMENT AND STABILIZATION

(71) Applicant: MediCarbone, Inc., Tucson, AZ (US)

(72) Inventors: Krishna Kolan, Tucson, AZ (US); Ravichandran Kollarigowda, Tucson, AZ (US); Neda Saadatmanesh, Tucson, AZ (US); Hamid Saadatmanesh, Tucson, AZ (US); Abiraman Srinivasan, Tucson, AZ (US)

(73) Assignee: MEDICARBONE, INC., Tucson, AZ (US)

( * ) Notice: Subject to any disclaimer, the term of this patent is extended or adjusted under 35 U.S.C. 154(b) by 0 days.

(21) Appl. No.: 18/312,408

(22) Filed: May 4, 2023

Related U.S. Application Data

(60) Provisional application No. 63/374,337, filed on Sep. 1, 2022, provisional application No. 63/374,319, filed on Sep. 1, 2022.

(51) Int. Cl.
*A61B 17/72* (2006.01)
*A61B 17/88* (2006.01)
*A61B 17/56* (2006.01)

(52) U.S. Cl.
CPC ...... *A61B 17/7258* (2013.01); *A61B 17/8836* (2013.01); *A61B 17/8858* (2013.01); *A61B 2017/564* (2013.01); *A61B 2017/568* (2013.01)

(58) Field of Classification Search
CPC ............ A61B 17/7258; A61B 17/8836; A61B 17/8858; A61B 2017/564; A61B 2017/568

USPC ........ 606/60, 262, 62, 63, 76, 77, 92–95, 99
See application file for complete search history.

(56) References Cited

U.S. PATENT DOCUMENTS

| | | | |
|---|---|---|---|
| 5,490,859 | A | 2/1996 | Mische et al. |
| 6,066,167 | A | 5/2000 | Lau et al. |
| 6,425,923 | B1 | 6/2002 | Stalcup et al. |
| 7,008,446 | B1 | 3/2006 | Amis et al. |
| 7,806,900 | B2 | 10/2010 | Rabiner |
| 7,968,616 | B2 | 6/2011 | Meyer et al. |

(Continued)

FOREIGN PATENT DOCUMENTS

| | | | |
|---|---|---|---|
| WO | 2021123413 A1 | 6/2021 | |

OTHER PUBLICATIONS

Wennergren et al. "Treatment and re-operation rates in one thousand and three hundred tibial fractures from the Swedish Fracture Register." European Journal of Orthopaedic Surgery & Traumatology 31 (2021): 143-154.

(Continued)

*Primary Examiner* — Tessa M Matthews
*Assistant Examiner* — David C Comstock
(74) *Attorney, Agent, or Firm* — NGUYEN TARBET LLC

(57) ABSTRACT

An orthopedic intramedullary sleeve apparatus for internal bone fixation for bone fracture treatment of a patient. The apparatus may comprise a multilayer sleeve component comprising one or more access valves disposed on a surface of the sleeve. Each access valve may comprise one or more resealable ports for injecting polymers or monomers or resins or any curable types of cement. The sleeve component may be positioned inside the intramedullary cavity in a minimally invasive way and removed from the intramedullary cavity.

24 Claims, 20 Drawing Sheets

(56) References Cited

U.S. PATENT DOCUMENTS

| | | | |
|---|---|---|---|
| 8,747,412 | B2 | 6/2014 | Bae et al. |
| 10,292,823 | B2 | 5/2019 | Rabiner et al. |
| 10,426,641 | B2 | 10/2019 | Clerc et al. |
| 11,324,614 | B2 | 5/2022 | Trollsas et al. |
| 11,413,170 | B2 | 8/2022 | Pereira et al. |
| 2009/0299374 | A1* | 12/2009 | Tilson ............... A61B 17/8833 606/94 |
| 2010/0076503 | A1 | 3/2010 | Beyar et al. |
| 2013/0023877 | A1 | 1/2013 | Rabiner et al. |
| 2013/0253661 | A1 | 9/2013 | D'Agostino et al. |
| 2014/0180288 | A1* | 6/2014 | DiPoto ............... A61B 17/7275 606/63 |
| 2014/0207145 | A1* | 7/2014 | Sennett ............ A61B 17/8811 606/93 |
| 2014/0277568 | A1 | 9/2014 | Baehre et al. |
| 2016/0015467 | A1 | 1/2016 | Vayser et al. |
| 2017/0239396 | A1* | 8/2017 | D'Agostino ....... A61B 17/7275 |
| 2019/0117848 | A9* | 4/2019 | D'Agostino .......... A61F 2/2846 |
| 2019/0357930 | A1 | 11/2019 | Cao et al. |
| 2022/0361928 | A1* | 11/2022 | D'Agostino ........... A61B 17/72 |

OTHER PUBLICATIONS

Murphy et al. "3D bioprinting of stem cells and polymer/bioactive glass composite scaffolds for bone tissue engineering." International Journal of Bioprinting 3.1 (2017).

Kolan et al. "Bioprinting with bioactive glass loaded polylactic acid composite and human adipose stem cells." Bioprinting 18 (2020): e00075.

Bone Grafting—OMF—Grafton Bone Graft | Medtronic. https://www.medtronic.com/us-en/healthcare-professionals/products/spinal-orthopaedic/bone-grafting.html retrieved from web on Aug. 28, 2023.

DBM | Stryker. https://www.stryker.com/us/en/trauma-and-extremities/products/dbm.html retrieved from web on Aug. 28, 2023.

Hertz, Audrey, and Ian J. Bruce. "Inorganic materials for bone repair or replacement applications." (2007): 899-918.

Hench, Larry L. "The story of Bioglass®." Journal of Materials Science: Materials in Medicine 17.11 (2006): 967-978.

Kolken, H. Ma, and A. A. Zadpoor. "Auxetic mechanical metamaterials." RSC advances 7.9 (2017): 5111-5129.

Saxena, Krishna Kumar, Raj Das, and Emilio P. Calius. "Three decades of auxetics research-materials with negative Poisson's ratio: a review." Advanced Engineering Materials 18.11 (2016): 1847-1870.

Karageorgiou, Vassilis, and David Kaplan. "Porosity of 3D biomaterial scaffolds and osteogenesis." Biomaterials 26.27 (2005): 5474-5491.

North, Michael A., Chelsey A. Del Grosso, and Jonathan J. Wilker. "High strength underwater bonding with polymer mimics of mussel adhesive proteins." ACS applied materials & interfaces 9.8 (2017): 7866-7872.

Park et al. "A wireless pressure sensor integrated with a biodegradable polymer stent for biomedical applications." Sensors 16.6 (2016): 809.

Reeves, Jennifer A., Michael L. Allegrezza, and Dominik Konkolewicz. "Rise and fall: poly (phenyl vinyl ketone) photopolymerization and photodegradation under visible and UV radiation." Macromolecular rapid communications 38.13 (2017): 1600623.

Yang et al. "Synthesis and Characterization of Hydroxy-telechelic Four-arm Star-shaped Oligo (tetrahydrofuran), Their Crosslinking, and Thermomechanical Investigation of the Poymer Network." MRS Online Proceedings Library (OPL) 1403 (2012): mrsf11-1403.

Van Renterghem, Lieven M., Eric J. Goethals, and Filip E. Du Prez. "Star-shaped poly (tetrahydrofuran) with reactive end groups: Design, MALDI-TOF study, and solution behavior." Macromolecules 39.2 (2006): 528-534.

Caroli, Giuseppe, and Katja Loos. "Functional end groups in polytetrahydrofuran." Macromolecular Chemistry and Physics 214.22 (2013): 2602-2606.

* cited by examiner

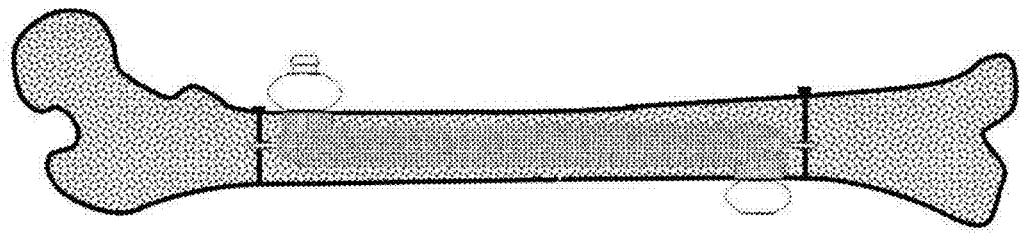
FIG. 1E
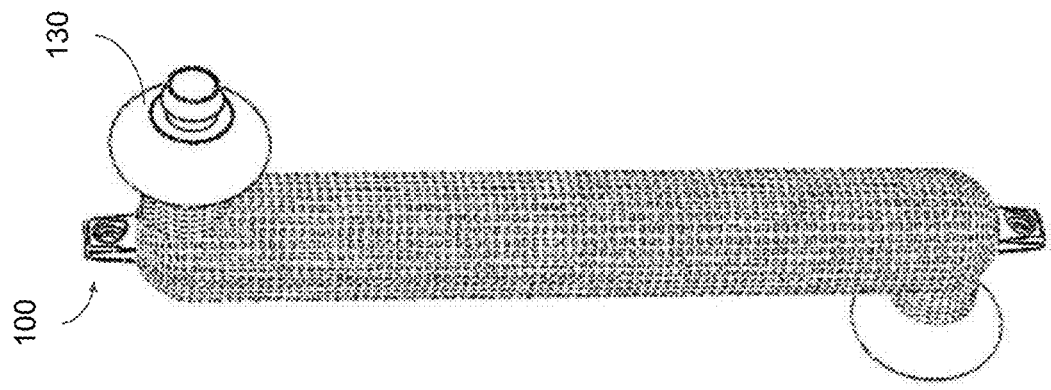
FIG. 1D
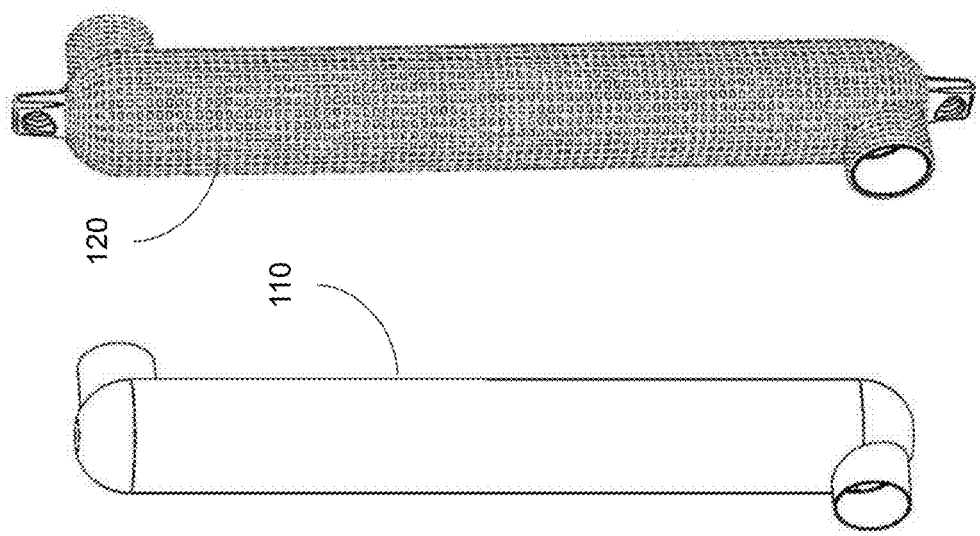
FIG. 1C
FIG. 1B
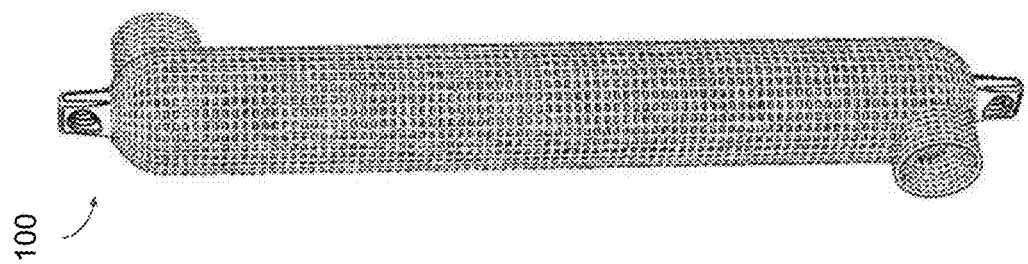
FIG. 1A

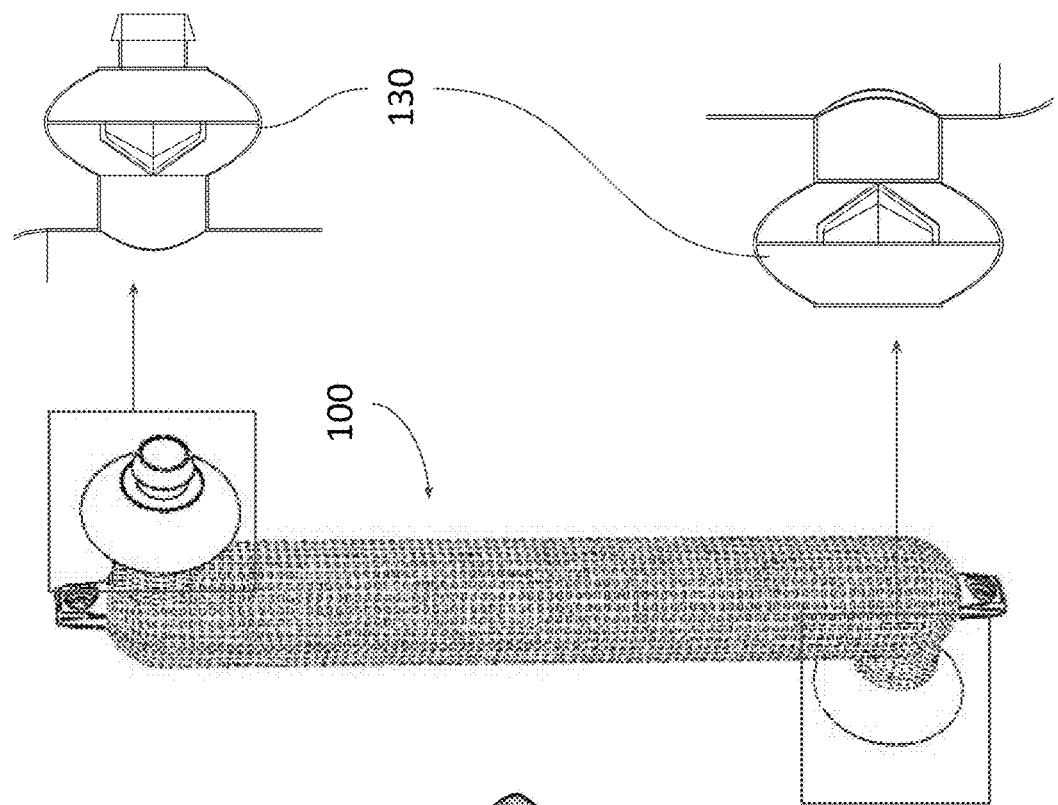
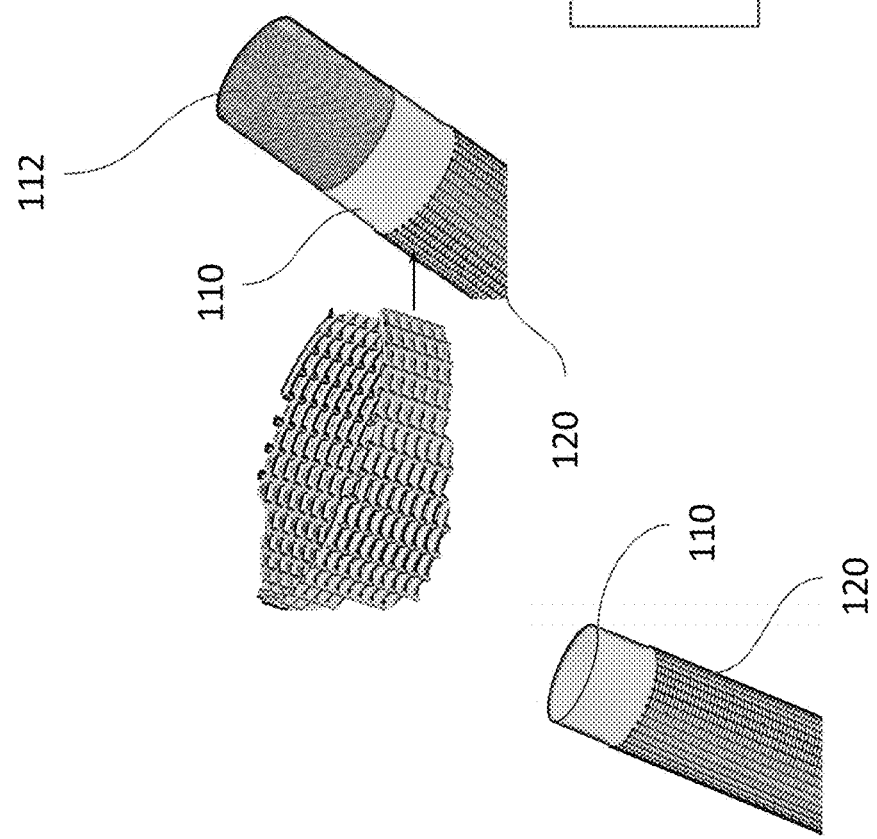
FIG. 2

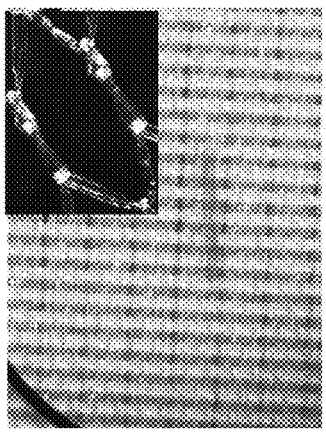
FIG. 4A
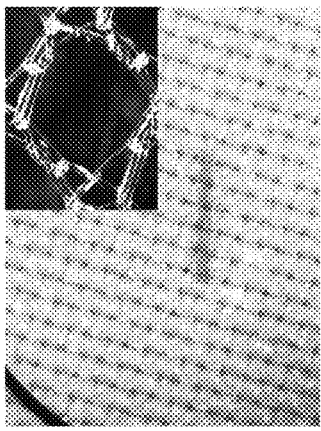
FIG. 4B
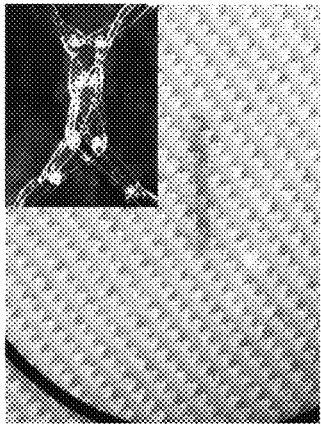
FIG. 4C
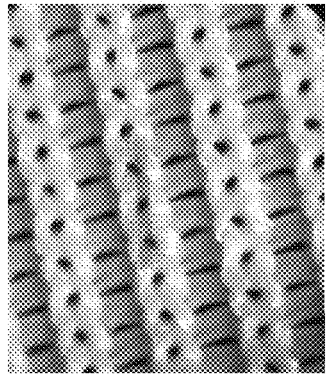
FIG. 4D
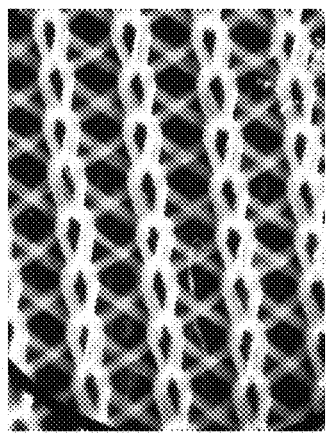
FIG. 4E
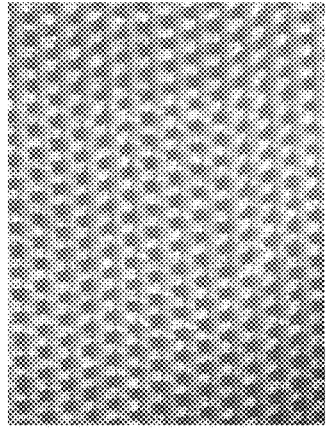
FIG. 4F
FIG. 4G
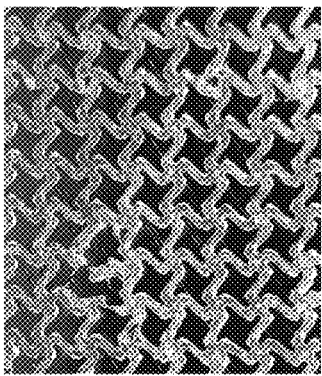
FIG. 4H

| Candidate materials | | | Membrane tensile testing | | Peel test - before (L) and after surface mod (R) | | 3-point testing of PMMA+sleeve pins | |
|---|---|---|---|---|---|---|---|---|
| Membrane | Thickness t (mm) | Density (g/cc) | Tensile Strength (MPa) | Modulus (GPa) | Strength (N) (load/mm) | Strength (N) (load/mm) | Flexural Strength (MPa) | Modulus (GPa) |
| EVA | 0.23 | 0.9 | 7-26 | 0.05 | 15 | 50 | 67 | 1.6 |
| UHMWPE | 0.25 | 0.9 | 65 | 0.93 | 0 | 10 | - | - |
| ePTFE | 0.23 | 0.22-1.52 | 20-45 | 0.39-0.6 | 10 | N/A | 33 | 0.34 |
| PMMA | | | - | - | - | - | 97 | 2.5 |
| PMMA+CF sleeve | | | - | - | 40 | N/A | 100-300 | 1-20 |
| Bone (trabecular)† | | | 0.03-65 | 1-10 | - | - | 10-140 | 1-10 |
| Bone (cortical)† | | | 50-130 | 15-20 | - | - | 50-280 | 6-14 |

† properties depend on age, sex, anatomical region (proximal, distal, or mid-diaphysis), and loading (trans. vs. long.) with the maximum for samples extracted from mid-diaphysis region and tested in longitudinal direction.

FIG. 5

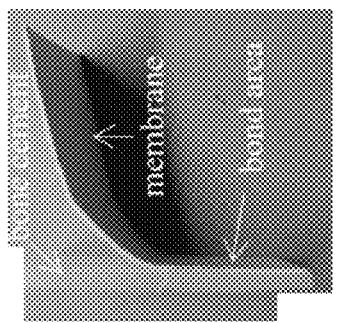
FIG. 7A
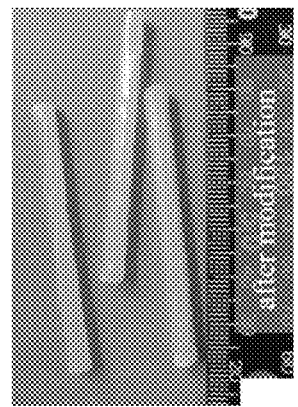
FIG. 7B
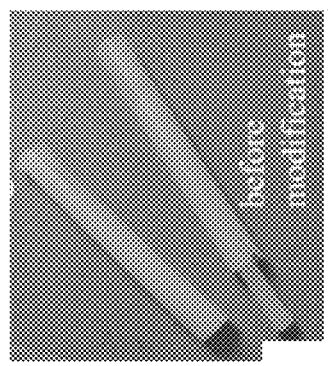
FIG. 7C
FIG. 7D
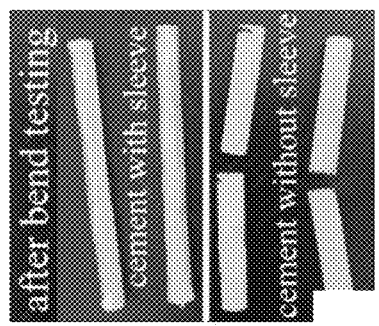
FIG. 7E

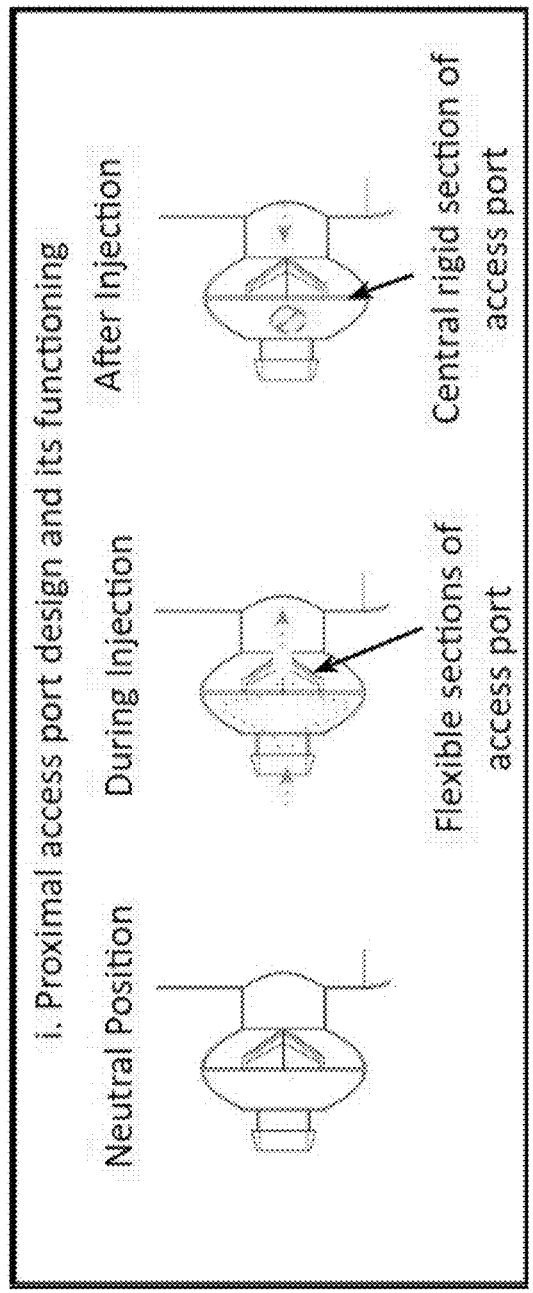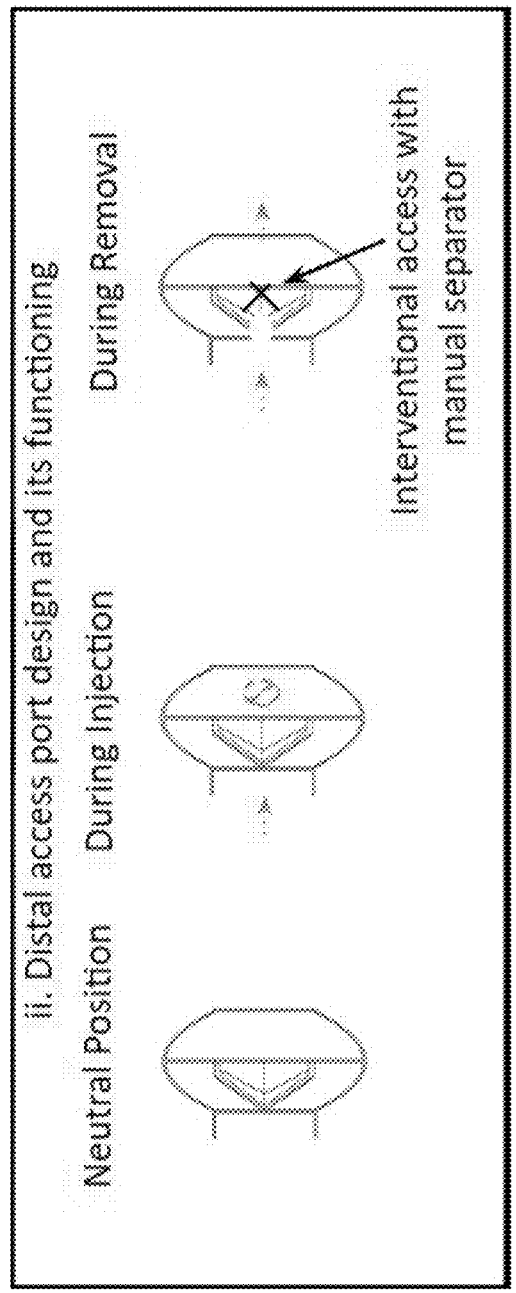
FIG. 11A
FIG. 11B

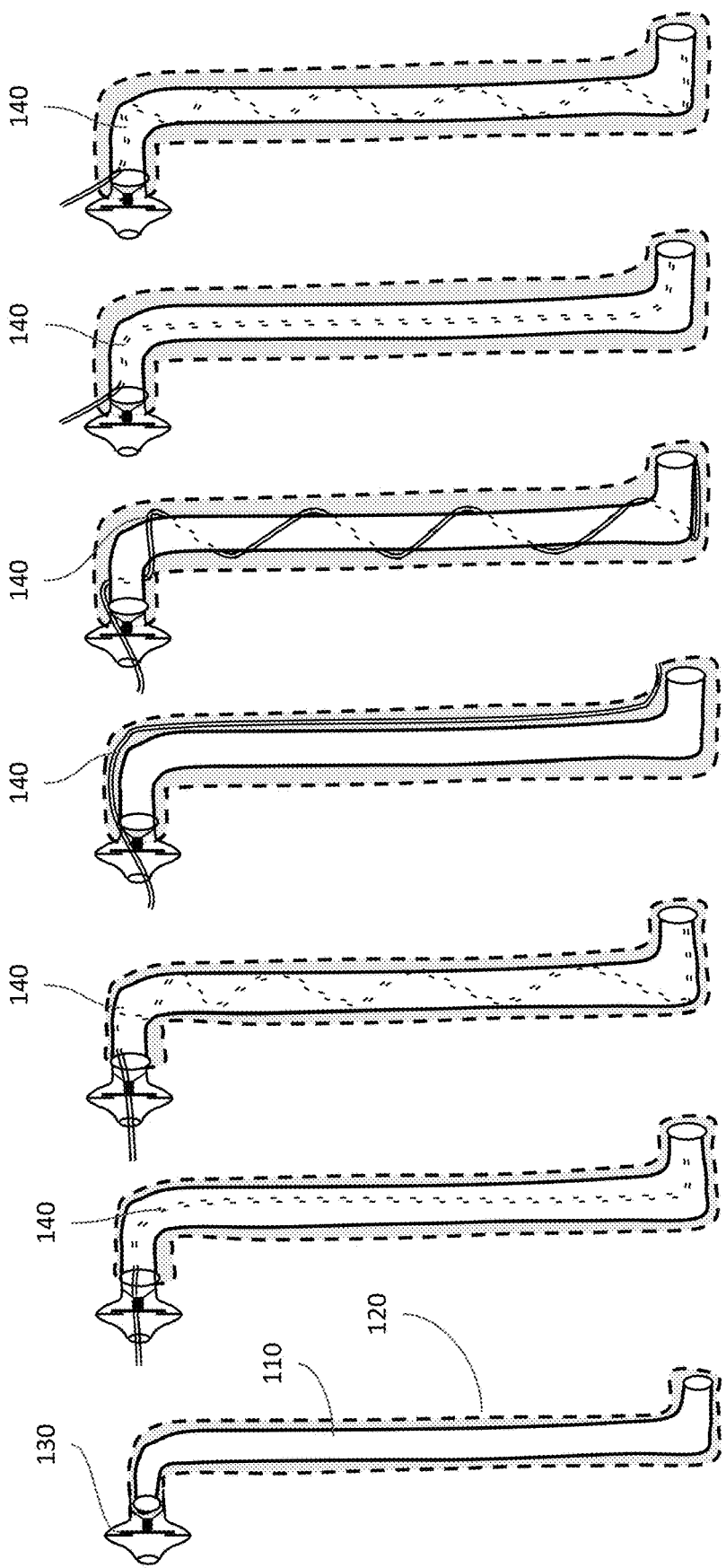

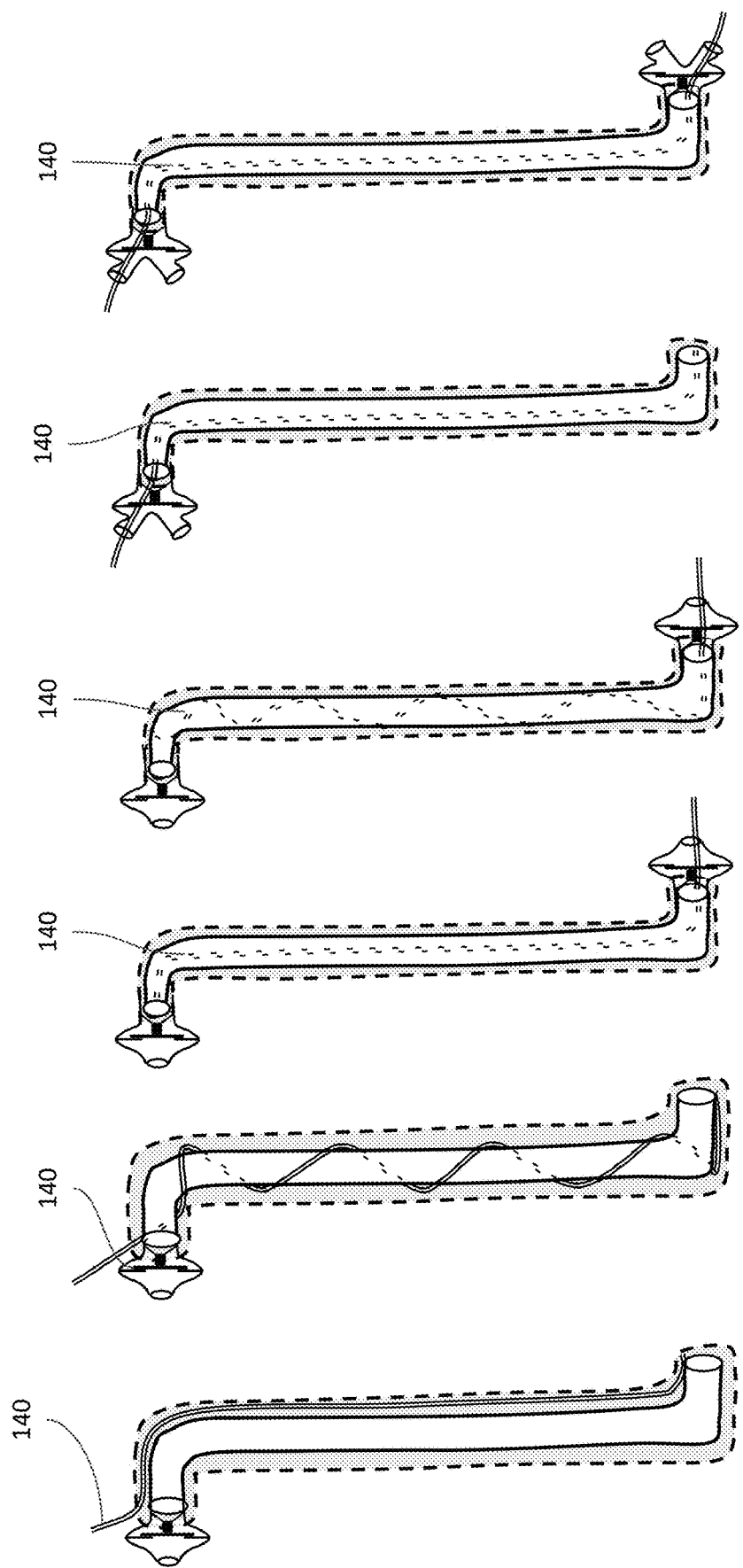

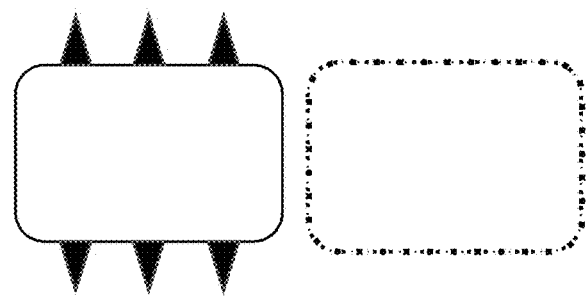
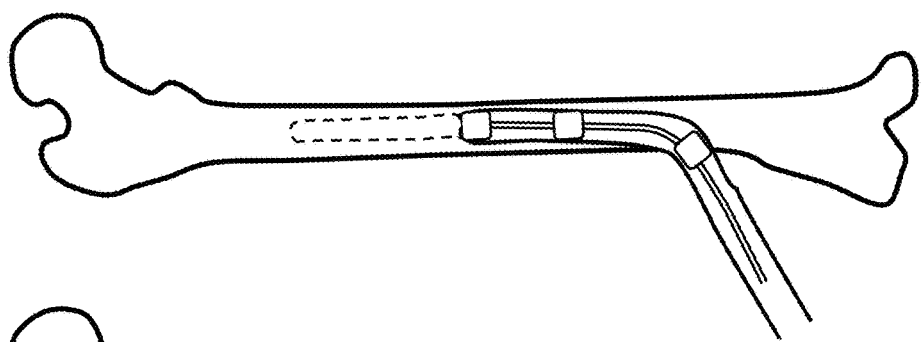
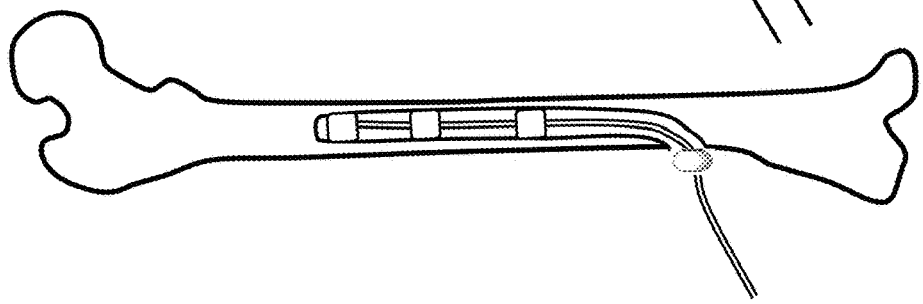
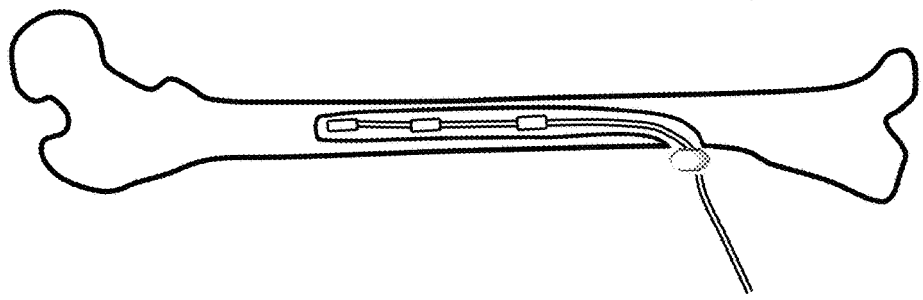
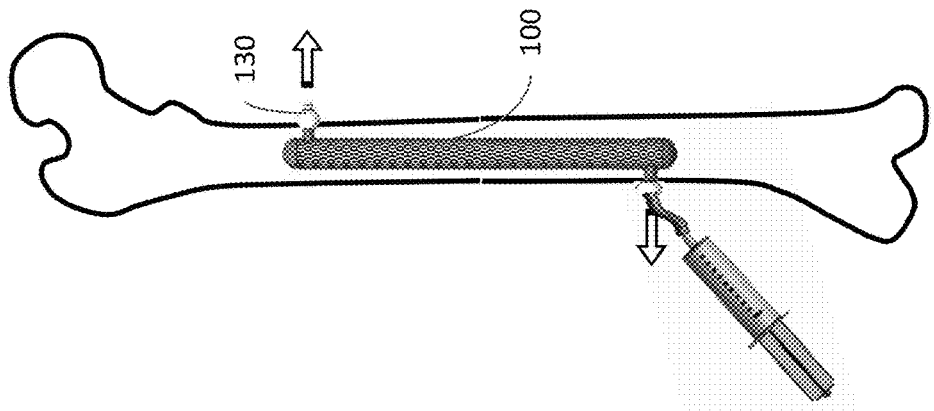
FIG. 13E
FIG. 13D
FIG. 13C
FIG. 13B
FIG. 13A

METHODS FOR CREATING, INSERTING, AND REMOVING AN INTRAMEDULLARY SLEEVE SYSTEM FOR BONE TREATMENT AND STABILIZATION

CROSS-REFERENCES TO RELATED APPLICATIONS

This application is a non-provisional and claims benefit of U.S. Provisional Application No. 63/374,319 filed Sep. 1, 2022 and U.S. Provisional Application No. 63/374,337 filed Sep. 1, 2022, the specifications of which are incorporated herein in their entirety by reference.

FIELD OF THE INVENTION

The present invention relates to implantable systems for bone repair, treatment, and stabilization that are typically performed using a minimally or less invasive method. More specifically, the present invention relates to intramedullary sleeve systems that are inserted into the bone during the procedure.

BACKGROUND OF THE INVENTION

A bone fracture is a medical condition where the continuity of the bone is broken. A significant percentage of bone fractures occur because of high-force impact or stress. However, a fracture may also be the result of medical conditions that weaken the bones, for example, osteoporosis, some cancers, or osteogenesis imperfecta.

Bone healing is a natural process that heals scarlessly. Fracture treatment is usually aimed at making sure there is the best possible function of the injured part after healing. Treatment also focuses on providing the injured bone with the best circumstances for optimum healing. For the natural healing process to begin, the ends of the broken bone need to be lined up; this is known as fracture reduction. After fracture reduction, the bones must stay aligned throughout the healing process and this is typically achieved using external fixation devices such as plaster casts or external fixators and(or) internal fixation using intramedullary nails, which are internal metal rods or flexible wire that are placed down the center of long bones; with or without metal plates and pins that go into the bone directly through the skin. This kind of treatment is the de facto gold standard preferred by orthopedic surgeons wherein the fractured limb is immobilized anywhere from 2 to up to 8 weeks depending on various factors including the type of bone affected, the patient's age, the existence of other complications, such as vascularization or an infection.

There is an immediate need to improvise the methods for fracture fixation or even prevent bone fractures in identified susceptible patients. Some common side effects of using existing metal implants including nails, plates, and screws are chronic inflammation, presence of metal debris in body fluids, patient discomfort because of screws, osteolysis, and implant loosening due to stress shielding caused by stiffer metallic material. Such side effects most commonly end up with revision surgeries in almost 30% of the patients even when considered for fractures affecting one particular bone. Therefore, the need of the hour is a minimally invasive bone fracture treatment procedure that can not only avoid such side effects and avert revision surgeries.

Almost all major bone fractures require some form of incision to allow bone alignment and insertion of stabilizing rods, attachment of brackets, etc. Such incisions typically create additional morbidity and often require extensive rehabilitation time.

U.S. Pat. No. 6,425,923 describes an orthopedic implant that includes a flexible bag having at least a portion thereof that is expandable under pressure; and a polymer within the bag. The orthopedic implant is implanted within a bone by forming a cavity in the bone; inserting a flexible bag into the cavity, the flexible bag having at least a portion thereof which is expandable under pressure; pressure filling the bag with a polymer, whereby the expandable portion of the bag expands to substantially fill the cavity in the bone; and hardening the polymer. In addition, U.S. Pat. App. No. 20100076503 describes a method of long bone strengthening and a composite implant for such strengthening (e.g., a plurality of rigid tensile rods, in a matrix of cement and surrounded by a partially porous bag). However, these, and other existing solutions fail to meet the need for a bone repair, strengthening system, and infection prevention system that is permanent (e.g., non-absorbable), while providing the option for removal and further fail to provide a customizable solution for each patient's need.

U.S. Pat. No. 9,320,601 B2 describes a method comprising forming a biodegradable composite implant formed by a reinforcing element and a containment bag. The implant is to be positioned entirely within a bone cavity, and the containment bag controls the degradation of the composite implant by modulating the ingress of fluid into the containment bag. U.S. Pat. No. 10,028,776 B2, U.S. Pat. No. 10,517,654 B2, and U.S. application Ser. No. 16/025,639 describe similar methods, all teaching the concept of biodegradable materials, complete encapsulation of the implant in the bone cavity, or both. However, the implementation of only biodegradable materials and full encapsulation of the implant within the bone in these patents greatly limits the potential customization and personalization of the implant in terms of materials used, as well as the potential methods for removal.

U.S. Pat. No. 10,52,169 B2 describes a bone implant comprising a rod serving as a reinforcement component and a degradable matrix serving as a sheet component. The rod and sheet are secured to one another to form a core structure of a bone implant. However, there are many inefficiencies in the insertion and removal of such a rod-sheet implant device. Furthermore, the variety of compatible bones is greatly diminished by the use of such a rigid system.

U.S. Pat. No. 10,525,169 B2 describes a composite structure comprising a plurality of reinforcement components, each in the form of a sheet. The plurality of sheet components are arranged in layers and form the core structure of the implant. However, the efficacy of an implant device comprising sheets alone may be unsuitable for most fracture repair applications. Furthermore, the implementation of a plurality of identical sheets limits the customizability and personalization of the implant.

There have been some approaches proposed by other researchers that focus on using certain surgical approaches to fix bone fractures. However, these approaches lack certain novel features that the present invention possesses in terms of designing implants that are removable in a less invasive fashion, being able to bond with the bone, and at the same time providing consistent structural support without compromising the mechanical properties. The present invention describes the intramedullary sleeve systems that form a crucial bridge between the fractured bone and the injected polymer in the in-situ created intramedullary rods. Provided herein is the intramedullary sleeve apparatus designed to hold and cure an injectable polymer system (in liquid, viscous and semi-solid forms) to form a seamless unit that supports surrounding bone tissue during bone fracture treatment.

BRIEF SUMMARY OF THE INVENTION

It is an objective of the present invention to provide systems and methods that allow for intramedullary sleeve systems that are inserted into the bone during the procedure, as specified in the independent claims. Embodiments of the invention are given in the dependent claims. Embodiments of the present invention can be freely combined with each other if they are not mutually exclusive.

The co-owned non-provisional applications, titled "A METHOD OF CREATING BIOCOMPATIBLE POLYMERIC RESIN SYSTEMS FOR BONE REPAIR AND MANAGEMENT" and "SYSTEMS AND METHODS FOR BONE REPAIR AND MANAGEMENT USING BIOCOMPATIBLE POLYMERIC RESIN", are incorporated herein in their entirety by reference.

The method includes the insertion of a thin multi-layered sleeve system or a uni-sleeve system containing one or more openings with valve systems that enable the insertion of the sleeve inside the bone cavity and the injection of a biocompatible polymer into the sleeve. In this manner, a very strong dowel is created inside the bone cavity bridging the sides of the fracture and conforming to the bone cavity. The systems and methods described herein eliminate the need for open cuts and result in significantly less trauma and recovery time. In addition, the lack of metal eliminates potential interference issues with imaging techniques such as MRI. The sleeve system described herein provides a configurable, modular, and patient-specific solution for the repair and strengthening of bones that can be left in place permanently or removed entirely or partially if desired. The multi-component sleeve system can be non-resorbable or some components can be made resorbable if desired. The sleeve system will enable controlled injection of liquid polymers, viscous polymers or resins, semi-solid resins, or acrylic-based bone cement without any air pockets. The sleeve system also enables the insertion of a diffusive light guide to cure the polymer and ultrasonic probes to pulverize the cured polymer.

For example, in some embodiments, provided herein is a method of treating or stabilizing (e.g., by strengthening a bone) a bone fracture or strengthening a bone in a subject, comprising: a) making at least one (e.g., 1, 2, 3, 4, or more) holes (e.g., on the mm scale in diameter) through a bone, wherein optionally a first of hole is placed on the proximal side of the bone fracture and an optional second hole is on the distal side of the bone fracture; and b) inserting a multi-layered sleeve (e.g., ultra-high molecular weight polyethylene braided sleeve sandwiched with a non-porous polytetrafluoroethylene) into a first hole (e.g., optionally between the first and second holes); and c) filling the tube with a biocompatible polymer. In some embodiments, the holes are drilled (e.g., using laparoscopy). In some embodiments, the multi-layered sleeve has another sandwiched layer of carbon fiber to provide sufficient strength for the load-bearing bone. In some embodiments, a multi-layered sleeve doesn't contain a non-porous element and the sleeve is porous. In some embodiments, a multi-layered sleeve doesn't contain the porous element and the entire sleeve is non-porous. In some embodiments, the sleeve system insertion comprises the steps of inserting it in the first hole and drawing it via a lead wire that exits the second hole. In some embodiments, the second hole is significantly smaller in comparison to the first hole. In some embodiments, the sleeve system is inserted through one hole using a guide wire and is positioned in place.

In some embodiments, the sleeve system is permanently placed in the bone. In some embodiments, the sleeve system is removable (e.g., by removing the cured polymer inside the sleeve). In some embodiments, the sleeve system is configured to match the structural (pore sizes, shapes, and overall porosity) and mechanical properties (load bearing or non-load bearing, stiffness, and elasticity) of the surrounding bone tissue. Such variations are achieved by selecting appropriate materials, fabrication processes, and sleeve designs.

In some embodiments, the subject has a fracture. In some embodiments, the subject is at increased risk of a fracture (e.g., due to overuse, injury, or disease (e.g., osteoporosis).

In some embodiments, the sleeve is made in a 3D shape matched to the cavity and inserted only around the fractured area in the distal region or in the proximal region. In some embodiments, the sleeve system has a 3D shape that enables its insertion in the proximal region, through the diaphyseal region, and until the distal region. To enable the insertion of such a 3D sleeve, the sleeve system has multiple valves or openings as required to navigate the insertion or removal using a series of smaller holes created through laparoscopy. In addition, the positioning guides of this 3D sleeve are specifically designed to enable the guiding of the 3D sleeve inside the bone cavity.

The present disclosure is not limited to a particular material or configuration of a multi-layered sleeve system. In some embodiments, the sleeve system is an ultrathin layer of carbon fabric with appropriately placed valves. In some embodiments, the sleeve system doesn't contain a valve and only contains an opening that is connected to the syringe through a tube to inject the polymer. After curing the polymer, the tubing is cut off. In some embodiments, the sleeve system is a multi (e.g., double, triple, or more) layer bag comprising external and internal layers. In some embodiments, the external layer is porous and the internal layer is non-porous. In some embodiments, the internal layer is porous and the external layer is non-porous. In some embodiments, the sleeve system comprises one or more surface modifications (e.g., electrochemical, chemical, thermal, discharge plasma, or radiation treatment). In some embodiments, the surface modifications comprise or are antimicrobial agents (e.g., cationic groups such as quaternary ammonium compounds, metal-based antimicrobials such as silver or bismuth, polymer-based antimicrobials such as polyhexamethylene biguanide and or oxidizing agents such as hydrogen peroxide). In some embodiments, the impregnated sleeve is kept at a lower than body temperature and when it is inserted into the body it will start to polymerize at the body temperature, which is higher than the storage temperature.

The illustration shown in FIGS. 1A-1E summarizes different components of one typical configuration out of several possibilities of the Intramedullary Sleeve System. IM Sleeve System is designed to enable controlled injection of polymer or resin or monomer or a combination thereof, contain injected polymer or resin or monomer or a combination thereof at required internal pressure, conform to the bone cavity or the intramedullary cavity and withstand the curing procedures and temperatures, prevent leakage of monomer or residual monomer or polymer after curing procedures, resist surface oxidation, is hemocompatible, promote osseointegration, prevent cell-mediated degradation, bacterial infection, sustain polymer removal process if needed by allowing insertion of external and mechanical accessories to remove cured polymer through access valves and access ports, and be collapsible and removable if needed. In addition, the IM sleeve is designed with unique properties that match:

1. Anatomy of the host tissue where the sleeve is implanted—to match the varied bone internal natural architecture, the porous layer of the sleeve system will be fabricated using an appropriate manufacturing process that provides required pore sizes, and shapes, and enables the usage of required material. In some embodiments, a 3D-shaped multi-layered sleeve system is manufactured by fabricating one layer using an electrospinning process to obtain the required surface porosity and sandwiching with an injection molded second layer to obtain a non-porous layer and thereafter assembling with other valve components. The host bone will determine the sleeve styling and the manufacturing process. For example, the sleeve will be fabricated using a filament braiding process to enable large pores (>500 μm) for the outer layer of the sleeve system when the sleeve system is in contact with the trabecular bone.
2. Have load-distributing properties like the bone—the stiffness of a single bone varies at different locations and the properties of different bones also vary depending on their skeletal functionality. To match the stiffness and load distribution ability of the sleeve system with that of the surrounding bone tissue, the selection of materials in the multilayered system plays a crucial role. For example, to match the high stiffness of the cortical bone in the diaphyseal region, one of the inner layers of the sleeve system will contain carbon fiber or a material that can achieve a good bonding with the injected polymer and provide mechanical properties similar to that of the cortical bone. In other areas of the bone, a polymeric sleeve system will be selected to heal the non-load-bearing bone.
3. They have properties that can be matched to the quality of the bone, age, and sex—the quality of bone differs with age and sex. In scenarios where it is essential to externally enable bonding with the bone where inherently bone lacks the capability to regenerate faster (such as in the geriatric population), the sleeves will be manufactured either with a polymer bioactive glass composite material, or entirely with a fibrous bioactive glass material, or a bioresorbable material, or a polymeric material coated with necessary proteins to trigger the bone regeneration process in the surrounding bone tissue. In addition to the material selection, another crucial aspect to match the properties is the selection of the manufacturing process. Some of the manufacturing processes for sleeve fabrication include electrospinning, 3D printing, braiding, weaving, knitting, injection molding, compression molding, sheet forming and ultrasonic welding, etc.
4. The sleeve properties are customized to the local macro and micro physiological milieu—in order to match the local macro and micro physiological environment, in addition to the fabrication processes, the surface characteristics of the sleeve system will be altered by doping with the required micronutrients, ions that facilitate the bone formation, loading with osteostimulative proteins to augment fracture repair and improve osseointegration.
5. The sleeve is designed to enable the removal of the injected biocompatible polymer or resin and eventually the entire portion of the sleeve or a partial portion of the sleeve in a minimally invasive fashion. For example, the inner sleeve can be removed without removing the outer sleeve.

One of the unique and inventive technical features of the present invention is the implementation of a multiport access valve comprising a port for injection of a curable material into the sleeve, and a port for accepting a light guide with a flexible plug. Without wishing to limit the invention to any theory or mechanism, it is believed that the technical feature of the present invention advantageously provides for efficient injection of curable material as well as efficient curing of the material through a light guide such that no light escapes due to the flexible plug. None of the presently known prior references or work has the unique inventive technical feature of the present invention.

Any feature or combination of features described herein are included within the scope of the present invention provided that the features included in any such combination are not mutually inconsistent as will be apparent from the context, this specification, and the knowledge of one of ordinary skills in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIGS. 1A-1E show an illustration of one type of embodiment of the intramedullary sleeve having two access valves for an intramedullary device for internal bone fixation. FIG. 1A shows an external porous sleeve with optional provisions for securing the device. FIG. 1B shows an internal non-porous sleeve. FIG. 1C shows an assembled intramedullary sleeve with both internal and external sleeves. FIG. 1D shows access valves for injecting polymer, ports for inserting accessories and tools and removing cured polymer. FIG. 1E shows an in-situ formed intramedullary device in the bone using the intramedullary sleeve and secured using nails at proximal and distal ends (if and as required).

FIG. 2 shows different aspects of the intramedullary sleeve system including distal and proximal interlocking provisions on the outer sleeve, the access valve with a one-way valve mechanism, and the external porous sleeve and internal non-porous sleeve.

FIG. 3 shows an illustration of different surface properties for the inner sleeve. 1. Bristles on the inner surface. 2. Roughened surface. 3. Surface porosity with nano to micron-sized pores. 4. Surface porosity on both sides of the inner sleeves. 5. Inner half of the thickness has reinforcements including carbon fiber. 6. A gradient reinforcement of nanoparticles radially throughout the sleeve thickness.

FIGS. 4A-4H show different types of porous structures that could be used for outer sleeves. FIGS. 4A-4C show different knit types that can create micro and macro porosity. FIGS. 4D-4E show stretchable knit fabrics that have the capability to stretch and adapt to the defect site and even grow with bone. FIG. 4F shows woven fabric with designed and uniform pores. FIG. 4G shows a microstructure of an electrospun fabric with surface porosity. FIG. 4H shows a 3D-printed auxetic mesh that can withstand its radial dimensions even as it allows longitudinal bone growth.

FIG. 5 shows a table of summarized physical properties of some candidate polymers for the intramedullary sleeve.

FIGS. 6A-6D show plasma treatment of intramedullary sleeve candidate polymer membranes with oxygen gas for 10 min at 45 W plasma power improved the water contact angle by introducing active carboxyl groups on the surface (increased elemental oxygen quantities are shown using black arrows) FIGS. 6A-6B show the results with an ethylene-vinyl acetate membrane (EVA). FIGS. 6C-6D show the results with an ultrahigh molecular weight polyethylene membrane (UHMWPE).

FIGS. 7A-7E show images showing membrane bonding and compatibility with acrylic resin. FIGS. 7A-7B show peel test specimens made with candidate membrane materials such as EVA and expanded polytetrafluoroethylene (e-PTFE). FIGS. 7C-7D show the separation of bone cement with a UHMWPE inner sleeve before surface modification and bonding after surface modification. FIG. 7E shows a sleeve holding the fractured acrylic resin pieces together after testing demonstrating that the sleeve can contain the fracture of acrylic resin.

Figure 9G:
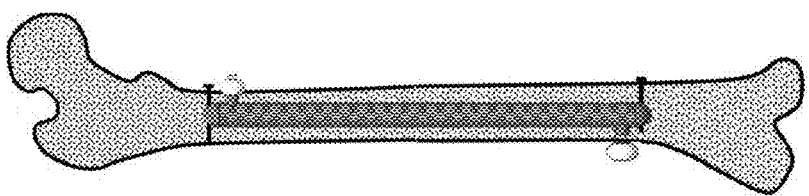
Figure 9F:
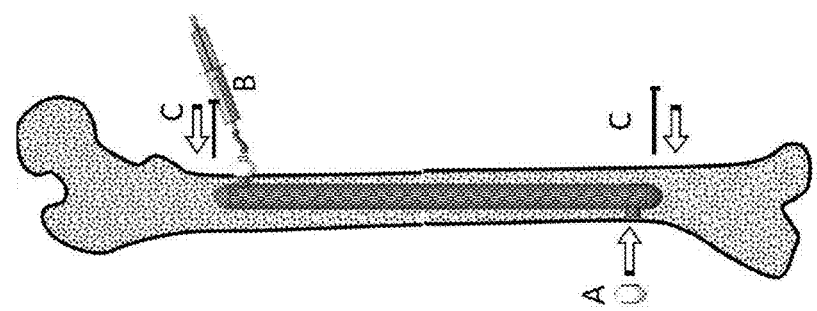
Figure 9E:
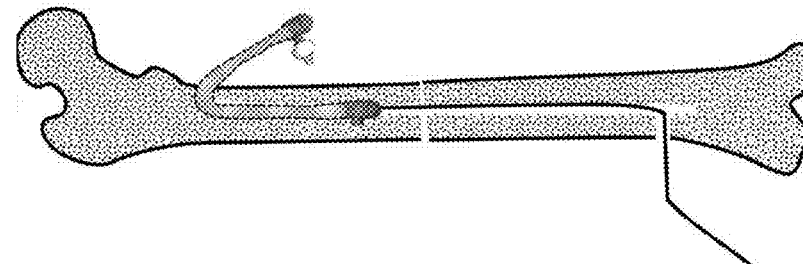
Figure 9D:
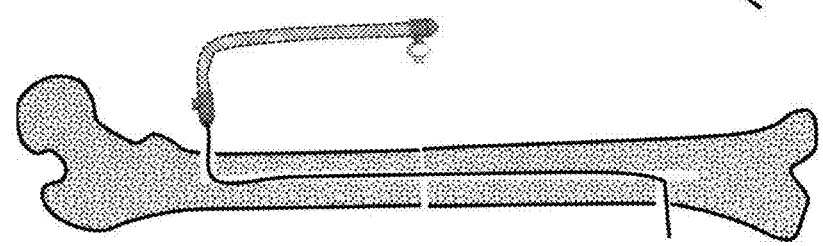
Figure 9C:
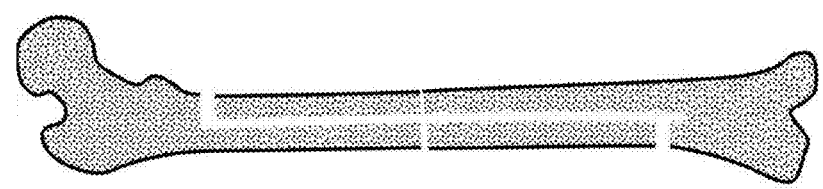
Figure 9B:
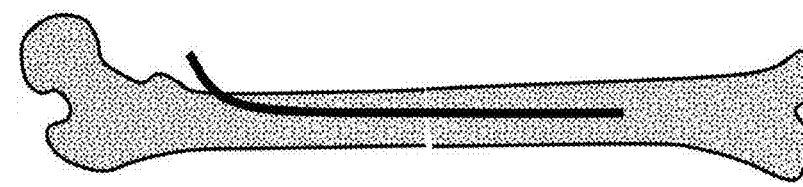
Figure 9A:
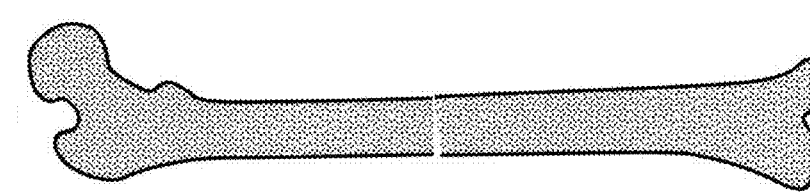

FIGS. 9A-9G show a schematic of an intramedullary sleeve insertion strategy in an embodiment wherein the distal end access valve is detachable and the proximal end access valve is attached to the sleeve. FIG. 9A shows an initial bone fracture. FIG. 9B shows intramedullary reaming to create space for the intramedullary sleeve. FIG. 9C shows the intramedullary space created for sleeve insertion and in-situ implant creation. FIGS. 9D-9E show the insertion of the sleeve component in the intramedullary space of the bone. FIG. 9F shows the sleeve distal end being enclosed with an access valve (A), injecting the polymer (B), and securing the implant with screws (C), if required. FIG. 9G shows the bone after the implant has been inserted into the intramedullary cavity generated by reaming.

Figure 10F:
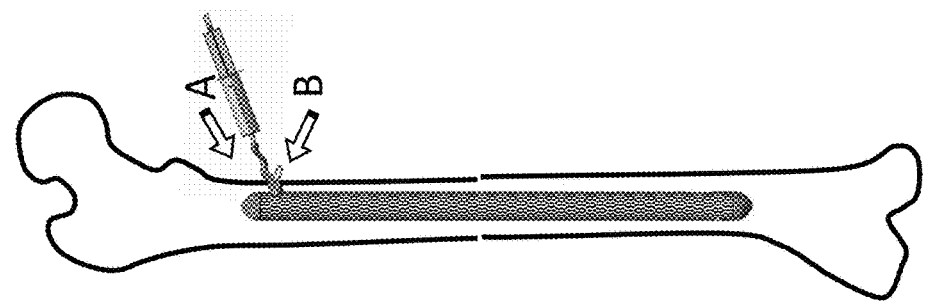
Figure 10E:
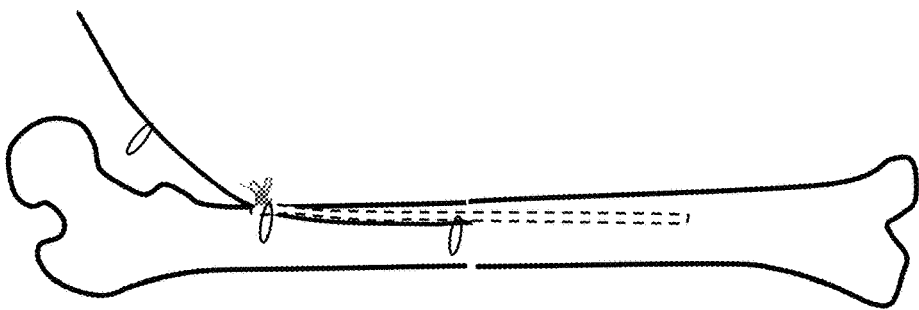
Figure 10D:
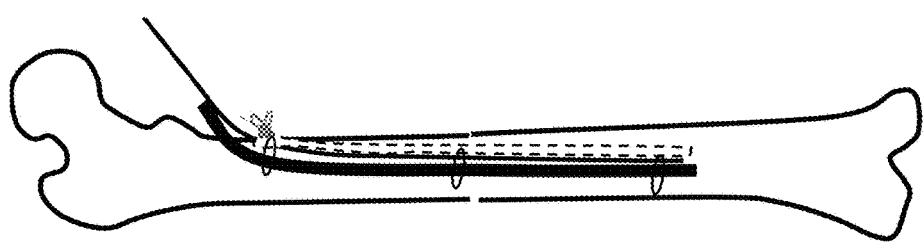
Figure 10C:
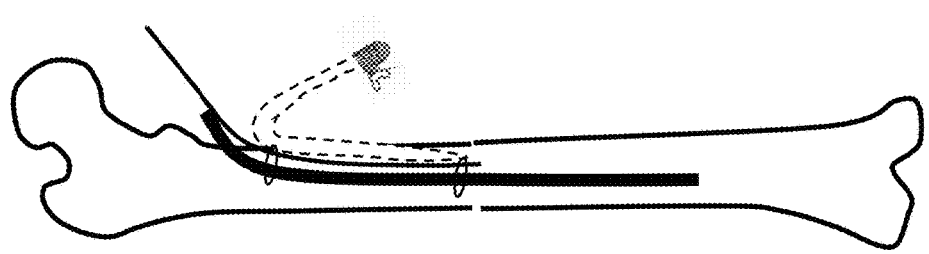
Figure 10B:
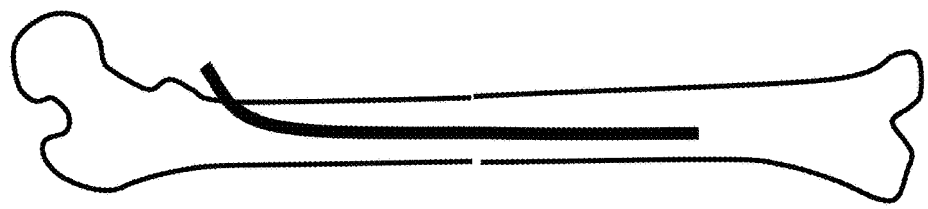
Figure 10A:
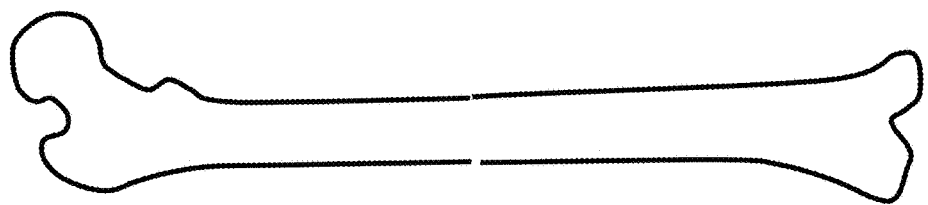

FIGS. 10A-10F show a schematic of the intramedullary sleeve insertion strategy in an embodiment wherein there is only a proximal end access valve attached to the sleeve. FIG. 10A shows the initial bone fracture. FIG. 10B shows guidewire placement with reaming of the intramedullary cavity. FIG. 10C shows intramedullary sleeve insertion using secondary positioning guide wire with a crochet hook to latch the sleeve and guide rings to direct the sleeve positioning. FIG. 10D-10E shows the removal of both guide wires and sleeve placement. FIG. 10F shows the injection of the polymer through one valve (A) of the access valve to form an in-situ IM device. The secondary valve (B) is for inserting light guides for polymerization and insertion of other accessories for cured resin removal.

Figure 11C:
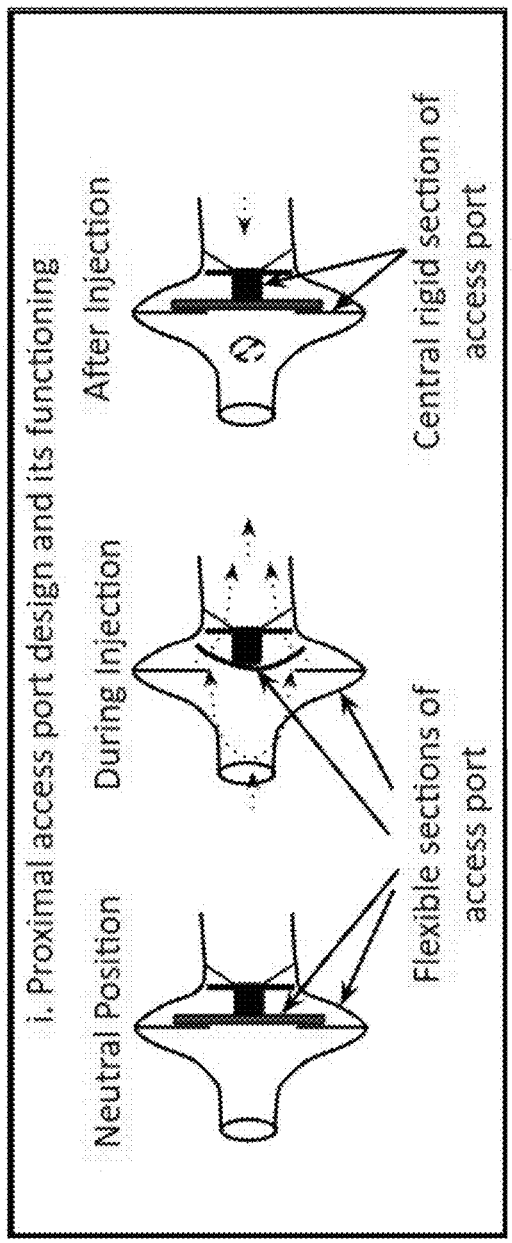
Figure 11D:
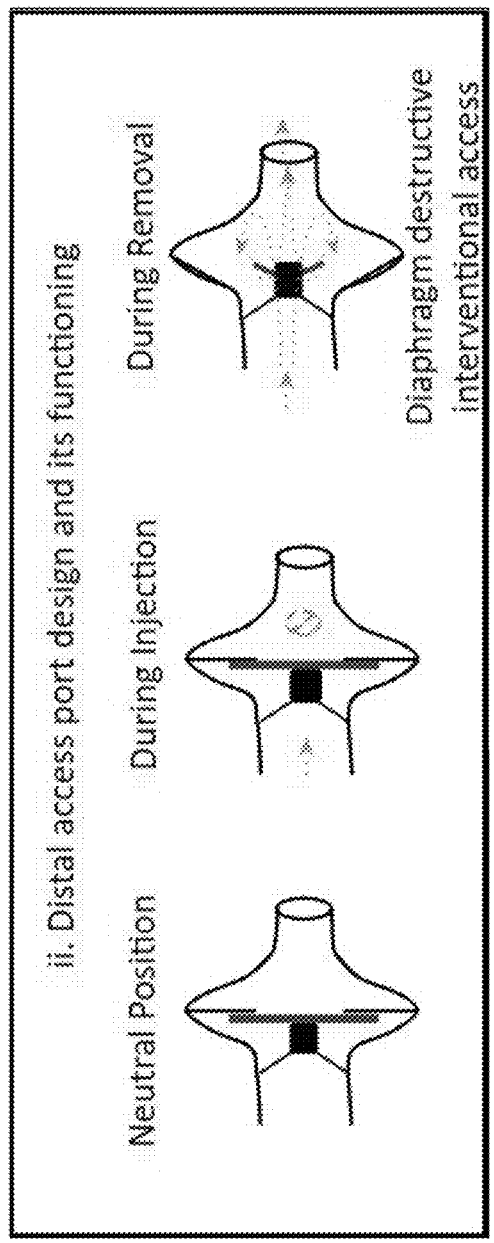

FIGS. 11A-11D show two examples of conventional IM sleeve access valve mechanisms. FIGS. 11A-11B show the duckbill valve mechanism employed at proximal and distal valves. FIG. 11A shows the valve function during polymer injection. FIG. 11B shows valve function during polymer removal. FIGS. 11C-11D show a diaphragm non-return valve mechanism employed at proximal and distal valves. FIG. 11C shows that the valve flaps only open at a predetermined pressure during polymer injection. FIG. 11D shows that the valve flaps are shut during injection and are manually opened using a separator after polymer depolymerization.

FIGS. 12A-12M show some possible placements of UV light source in the intramedullary sleeve system to enable injection of curable material through the valve mechanism opening present in the access valve. FIG. 12A shows an embodiment without any light guide in the intramedullary sleeve system. FIGS. 12B-12C show an embodiment where the light guide enters through the proximal valve. FIG. 12B shows an embodiment where the light guide passes straight through the internal sleeve. FIG. 12C shows an embodiment where the light guide is a spiral inside the internal sleeve. FIGS. 12D-12E show an embodiment where the light guide enters through the proximal valve. FIG. 12D shows the light guide passing through the internal-external sleeve interface. FIG. 12E shows the light guide as a spiral on the outside of the internal sleeve. FIGS. 12F-12G show an embodiment where the light guide enters through the proximal access valve-sleeve interface. FIG. 12F shows the light guide passing straight through the internal sleeve. FIG. 12G shows the light guide as a spiral inside the internal sleeve. FIGS. 12H-12I show an embodiment where the light guide enters through the proximal access valve-sleeve interface, and (FIG. 12H) passes longitudinally between sleeves or (FIG. 12I) passes as a spiral between sleeves. FIGS. 12J-12K show an embodiment where the light guide enters through the distal access valve. FIG. 12J shows an embodiment where the light guide passes straight through the internal sleeve. FIG. 12K shows an embodiment where the light guide is a spiral inside the internal sleeve. FIG. 12L shows an embodiment where the light guide enters through the dedicated light guide opening (secondary opening) of the proximal access valve and passes straight through the internal sleeve. FIG. 12M shows an embodiment where two light guides enter through their dedicated secondary openings on proximal and distal access valves.

FIGS. 13A-13E show a non-limiting embodiment of an intramedullary sleeve removal strategy. FIG. 13A shows application of light energy to the implant region, extraction of cured polymer from the inner sleeve, and removal of access valves. FIG. 13B shows the insertion of a catheter with inflatable balloons (B) through the distal access valve and port into the inner sleeve. FIG. 13C shows inflated balloons with pressurized air to grip and lock the sleeve. FIG. 13D shows the removal of the sleeve through the distal end of the bone. FIG. 13E shows two possible external surface provisions on the inflated balloons (top) sharp protrusions and (bottom) roughened surface with coated adhesive.

Figure 14B:
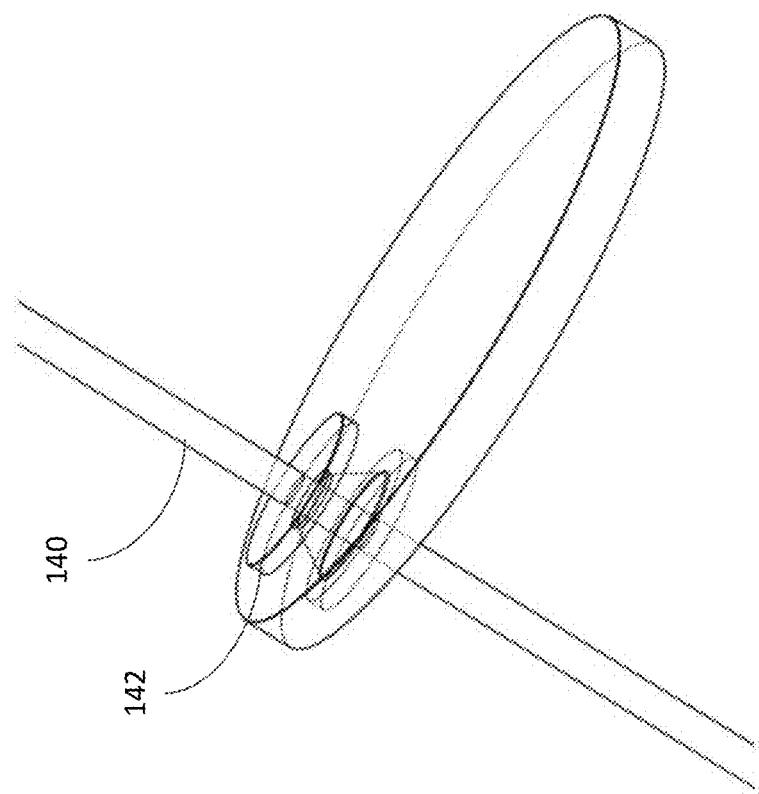
Figure 14A:
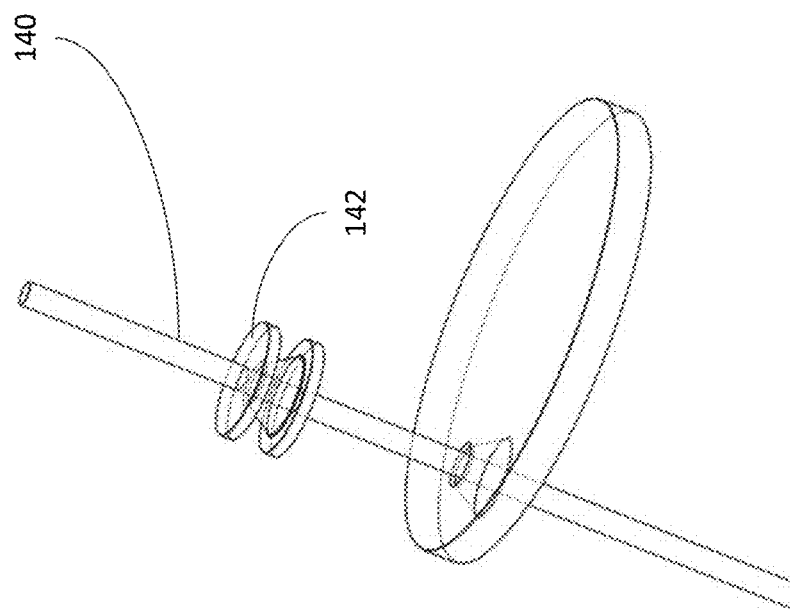
Figure 14D:
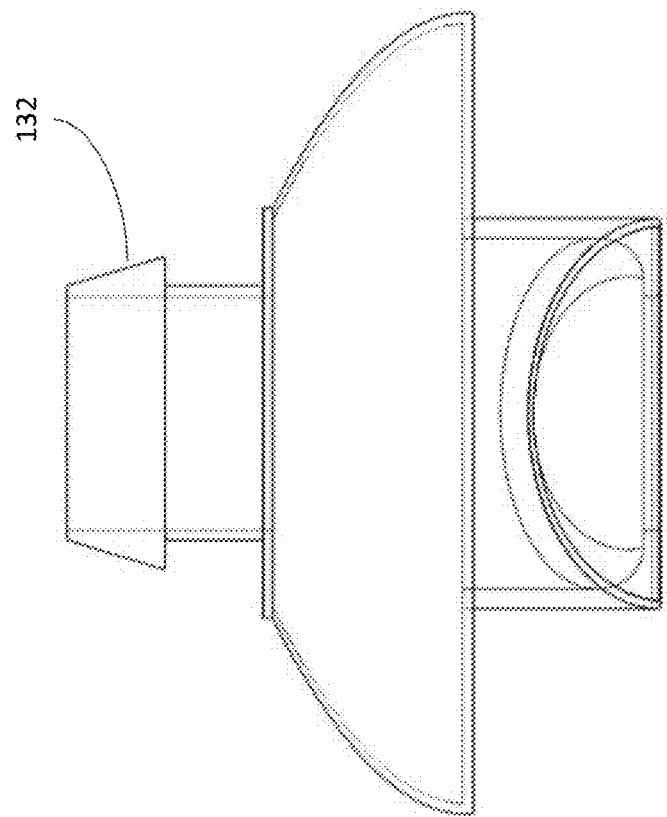
Figure 14C:
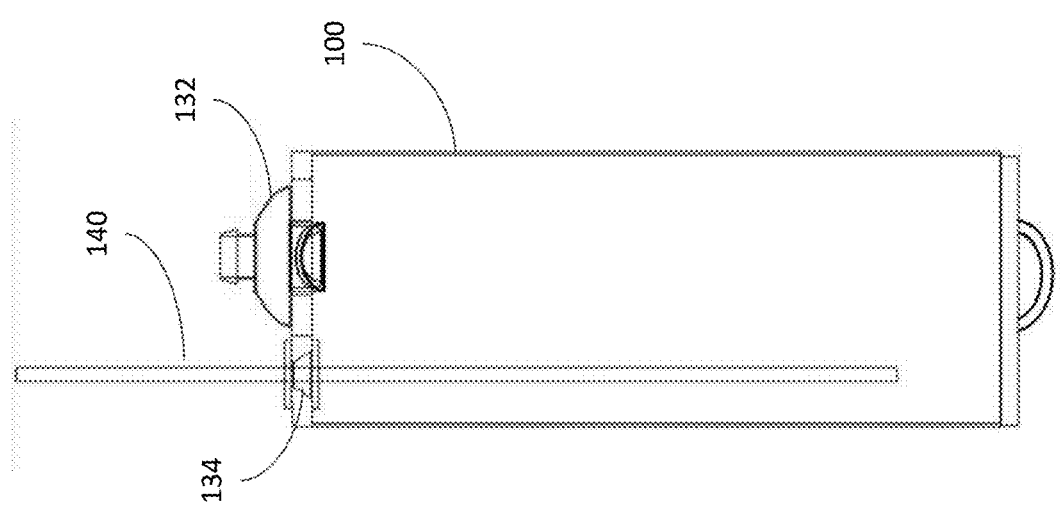

FIGS. 14A-14D show an embodiment of the multiport valve for injection of a curable material and insertion of a light guide comprising a flexible plug. FIG. 14A shows the multiport valve with the light guide partially inserted. FIG. 14B shows the multiport valve with the light guide fully inserted. FIG. 14C shows the multilayer sleeve device of the present invention having the multiport valve with the light guide fully inserted. FIG. 14D shows the curable material injection port of the multiport valve.

DETAILED DESCRIPTION OF THE INVENTION

Following is a list of elements corresponding to a particular element referred to herein:
- 100 apparatus
- 110 inner sleeve
- 120 outer sleeve
- 130 access valves
- 132 first port

134 second port
140 light guide
142 flexible plug

Referring now to FIGS. 1A-1E, the present invention features an intramedullary sleeve apparatus (100) configured to hold and cure injectable bone cement, polymerized polymer, or a combination thereof to form an intramedullary device that supports a surrounding bone during bone fracture treatment. In some embodiments, supporting the bone may comprise bonding to the bone. In some embodiments, the apparatus (100) may comprise an inner non-resorbable intramedullary sleeve (110) having one or more access valves (130) disposed through the inner sleeve (110) and an outer intramedullary sleeve (120) having at least one proximal end and at least one distal end. Each access valve may comprise one or more resealable ports and may allow access to the inner sleeve (110). Each access valve may be disposed at at least one proximal end of the inner sleeve (110) and the outer sleeve (120), at least one distal end of the inner sleeve (110) and the outer sleeve (120), or a combination thereof.

The inner sleeve (110) and the outer sleeve (120) may be bonded together. In some embodiments, the inner sleeve (110) and the outer sleeve (120) are bonded together by chemical bonding, physical bonding, or any method that causes the inner sleeve (110) and the outer sleeve (120) to be bound together. In some embodiments, the inner sleeve, and outer sleeve are bonded only at the ends that meet the access valves together with the access valve in such a way that a multilayered sleeve together with the access valve will act as one unified sleeve system. The length and diameter of the sleeve system are dependent on the fracture being treated in terms of size and the bone it is located on. In some embodiments, a thickness of the inner sleeve (110) may be 10 to 1000 μm. In some embodiments, a thickness of the outer sleeve (120) may be 10 to 1000 μm.

In some embodiments, the inner sleeve (110) may comprise a non-porous sleeve. In some embodiments, the outer sleeve (120) may comprise a porous sleeve or a non-porous sleeve. In some embodiments, the outer sleeve (120) may be fabricated with one or more biocompatible materials. Examples of biocompatible materials include but are not limited to natural hydrogels, synthetic hydrogels, demineralized and decellularized bone, carbon fiber, polymer composites, bioceramics, bioactive glasses, glass-ceramics, polymer bioactive glass composites, poly(acrylonitrile), poly(6-aminocaproic acid), poly(decamethylene adipamide), Nylon 10,6, Poly(etheretherketone), PEEK, Poly (ethylene terephthalate), PET, poly(hexamethylene adipamide), Nylon 6,6, poly(hexamethylene suberamide), Nylon 6,8, poly(styrene), poly(4-methylpentene), high-density polyethylene, ultra-high-molecular-weight polyethylene, polytetrafluoroethylene PTFE, expanded PTFE, modified ethylene-vinyl acetate, modified polyester of homopolymer or co-polymers, block copolymers, pebax, nylon, or a combination thereof.

In some embodiments, the inner sleeve (110) may be fabricated with one or more non-resorbable biocompatible materials. Examples of non-resorbable biocompatible materials include but are not limited to carbon fiber, and polymer composites, non-resorbable materials such as dense PTFE, expanded PTFE, PET, PEEK, titanium mesh, and titanium-reinforced polytetrafluoroethylene of a single material, or a combination thereof.

In some embodiments, the outer sleeve (120) and the inner sleeve (110) may be surface modified for osseointegration with the host tissue, anti-microbial property, load drugs, growth factors, peptides, and small molecules to induce bone growth in diseased bone of osteoporotic and geriatric patients, or a combination thereof. The outer sleeve (120) and the inner sleeve (110) may be surface modified by plasma surface treatment, a glow discharge method, chemical surface modification, coatings, radiation, lithography, and application of rough surfaces achieved by means of different fabrication techniques, or a combination thereof.

In some embodiments, the inner sleeve (110) may comprise an inside lining of carbon fiber or carbon-based material, metal fiber or metal-based mesh, glass fiber or glass-based mesh, or a combination thereof. In some embodiments, the inner sleeve (110) may comprise sensors built into an outer surface of the inner sleeve (110) to quantify the stress and motion between the inner sleeve (110) and the outer sleeve (120), and the intramedullary apparatus (100) and the surrounding bone. In some embodiments, the apparatus (100) may further comprise fixation provisions at at least one proximal end and at least one distal end to attach external fixation devices for securing the apparatus (100) to the surrounding bone.

In some embodiments, an access valve (130) of the one or more access valves comprises a first port (132) to allow for injection of a curable material, and a second port (134) to allow insertion of a light guide (140). The light guide (140) may be disposed through the second port (134) of the access valve (130) and may comprise a flexible plug (142) configured to seal the light guide (140) in the second port (134) of the access valve (130).

In some embodiments, the apparatus (100) may be fabricated to match an overall three-dimensional shape of a bone cavity of the surrounding bone. In some embodiments, the IM sleeve apparatus is manufactured in oversized dimensions so that the apparatus expands and conforms to the bone cavity considering the varying intramedullary space of the bone or in any bone cavity. In some embodiments, the IM sleeve apparatus is manufactured with materials and design in such a manner that both the inner and outer sleeves could expand as required and conform to the bone cavity to provide a natural load distribution and function (mechano-anatomical unit).

The present invention features an orthopedic intramedullary sleeve apparatus (100) for internal bone fixation for bone fracture treatment of a patient. In some embodiments, the apparatus (100) may comprise a multilayer sleeve component comprising one or more access valves disposed on a surface of the sleeve. Each access valve may comprise one or more resealable ports for injecting polymers, monomers, resins, or any curable types of cement. In some embodiments, the one or more ports may be shaped and configured based on their purpose or the tools that will be implemented in conjunction with them. The sleeve component may be positioned inside the intramedullary cavity in a minimally invasive way and removed from the intramedullary cavity. In some embodiments, each layer of the multilayer sleeve component may differ from all others in terms of materials, properties, or a combination thereof.

In some embodiments, the sleeve component may comprise an inner sleeve (110) and an outer sleeve (120). In some embodiments, one or more properties of the inner sleeve (110) and the outer sleeve (120) may be determined based on the bone mass index of the patient. In some embodiments, the apparatus may further comprise one or more sensors disposed on an outer surface of the outer sleeve (120), the inner sleeve (110), or a combination thereof. Each sensor of the one or more sensors may be capable of measuring pressure, stress, strain, temperature, or a combination thereof with respect to the sleeve component and the bone.

Referring now to FIGS. 9A-9G, the present invention features a method for applying an intramedullary sleeve apparatus (100) to a fractured bone to bond to the bone during bone fracture treatment. The method may comprise providing the intramedullary sleeve comprising an inner non-resorbable intramedullary sleeve having one or more access valves (130) disposed through the inner sleeve (110) and an outer intramedullary sleeve (120) having at least one proximal end and at least one distal end. The inner sleeve (110) and the outer sleeve (120) may be bonded together.

Each access valve may comprise one or more resealable ports and may allow access into the inner sleeve (110). Each access valve may be disposed at at least one proximal end of the inner sleeve (110) and the outer sleeve (120), at least one distal end of the inner sleeve (110) and the outer sleeve (120), or a combination thereof. The method may further comprise creating one or more keyholes through a cortical layer of the bone at at least one distal end and at least one proximal end of the bone, inserting one or more guide wires into the bone cavity as required, positioning the intramedullary sleeve within the bone cavity using one or more positioning guides between the one or more keyholes and through the bone.

The present invention features a method for creating an intramedullary fixation device in-situ to treat and prevent bone fractures. Provided herein is the intramedullary sleeve apparatus designed to hold and cure acrylic injectable polymer cement to form an intramedullary device that supports surrounding bone tissue during bone fracture treatment. Supporting the surrounding bone may comprise bonding to the bone. The intramedullary sleeve system may comprise an inner non-porous non-resorbable intramedullary sleeve having access valve(s) at the at least one proximal end (or) distal end (or) both proximal and distal end (or) any other region of the sleeve, and an outer porous or non-porous intramedullary sleeve having proximal and distal ends and having access valves adjacent to the at least one proximal end (or) a distal end (or) both proximal and distal ends.

The access valve adjacent to the at least one proximal end may face the lateral side and the access valve adjacent to the distal end may face the medial side (or) the access valves adjacent to both proximal and distal ends face the lateral side. The inner non-porous and outer porous sleeves may be bonded together. In some embodiments, the inner sleeve (110) and the outer sleeve (120) are bonded together by chemical bonding, physical bonding, or any method that causes the inner sleeve (110) and the outer sleeve (120) to be bound together.

The present invention features a method to treat and prevent bone fractures using a custom-designed in-situ cured fixation device matching the patient's intramedullary device comprising providing an intramedullary sleeve containing much of its body along the longitudinal axis (length of the bone) that has the capability to expand to take shape of the bone cavity. The proximal and distal ends of the aforementioned sleeve may contain projected openings one at each end or one opening at either end. The projected openings may be at an angle to the aforementioned longitudinal axis of the sleeve and have the capability to expand to take the shape of the bone cavity. The sleeve may further comprise a valve system that enables pressurized filling of bone cement into the sleeve located on the aforementioned access valve and in proximity to the external bone.

In some embodiments, the intramedullary sleeve comprises an outer porous or non-porous sleeve and an inner non-porous sleeve. In some embodiments, the outer sleeve can be fabricated with either resorbable or non-resorbable biocompatible materials. Examples of biocompatible materials include but are not limited to natural hydrogels, synthetic hydrogels, demineralized and decellularized bone, carbon fiber, polymer composites, bioceramics, bioactive glasses, glass-ceramics, polymer bioactive glass composites, poly(acrylonitrile), poly(6-aminocaproic acid), poly(decamethylene adipamide), Nylon 10,6, Poly(etheretherketone), PEEK, Poly(ethylene terephthalate), PET, poly(hexamethylene adipamide), Nylon 6,6, poly(hexamethylene suberamide), Nylon 6,8, poly(styrene), poly(4-methylpentene), high density polyethylene, ultra-high-molecular-weight polyethylene, polytetrafluoroethylene PTFE, expanded PTFE, modified ethylene-vinyl acetate, modified polyester of homopolymer or co-polymers, block copolymers, or a combination thereof.

In some embodiments, the inner sleeve can be fabricated with non-resorbable biocompatible materials. Examples of non-resorbable biocompatible materials include but are not limited to carbon fiber, and polymer composites, non-resorbable materials such as dense PTFE, expanded PTFE, titanium mesh, and titanium-reinforced polytetrafluoroethylene of a single material, poly(acrylonitrile), poly(6-aminocaproic acid), poly(decamethylene adipamide), Nylon, Poly(etheretherketone) (PEEK), Poly(ethylene terephthalate) (PET), Polyurethane, PEBAX, poly(hexamethylene adipamide), poly(hexamethylene suberamide), poly(styrene), poly(4-methylpentene), high density polyethylene, ultra-high-molecular-weight polyethylene (UHMWPE), polytetrafluoroethylene PTFE, expanded PTFE, ethylene-vinyl acetate (EVA), modified EVA, polyvinylidene fluoride (PVDF), polyvinyl chloride (PVC), modified polyester of homopolymer or co-polymers, block copolymers, or a combination thereof.

The present invention features an intramedullary sleeve apparatus (100) configured to hold and cure injectable bone cement, polymerized polymer, or a combination thereof to form an intramedullary device that conforms to the bone cavity and supports a bone during bone fracture treatment. In some embodiments, the apparatus (100) may comprise an inner non-resorbable intramedullary sleeve (110), having at least one proximal end and at least one distal end. An interior of the inner sleeve (110) may comprise a reinforcing material (112). The apparatus (100) may further comprise one or more access valves (130) disposed through the inner sleeve (110) so as to allow access into the inner sleeve (110). Each access valve may be disposed at at least one proximal end of the inner sleeve (110), at least one distal end of the inner sleeve (110), or a combination thereof. An access valve (130) of the one or more access valves may comprise a first port (132) to allow for injection of a curable material, and a second port (134) to allow insertion of a light guide (140). The apparatus (100) may further comprise the light guide (140) disposed through the second port (134) of the access valve (130), the light guide (140) comprising a flexible plug (142) configured to seal the light guide (140) in the second port (134) of the access valve (130). The apparatus (100) may be configured to be removed by external accessories.

In some embodiments, a method for removing the apparatus (100) from the bone after removal of cured resin may comprise inserting a mechanically operated tool having a hook in a closed position through an access valve of the one or more access valves (130) until it reaches an end of the apparatus (100), releasing the hook and engaging the apparatus (100) through physical piercing, and pulling the tool out of the bone through the access valve. In some embodiments, the tool may comprise a hook.

In other embodiments, a method for removing the apparatus (100) from the bone after removal of cured resin may comprise inserting a high vacuum hose through an access valve of the one or more access valves (130) until it reaches an end of the apparatus (100), and actuating the high vacuum hose such that the apparatus (100) is sucked out of the bone through a laparoscopy hole.

In some embodiments, the inner sleeve (110) may comprise a non-porous sleeve. The apparatus (100) may further comprise an outer intramedullary sleeve (120) disposed around the inner sleeve (110), having at least one proximal end and at least one distal end. The outer sleeve (120) may comprise a porous sleeve or a non-porous sleeve. An outer surface of the outer sleeve (120) directly in contact with the bone cavity may be surface modified for osseointegration with the host tissue, anti-microbial property, load drugs, growth factors, peptides, small molecules to induce bone growth in diseased bone, osteoporotic, and geriatric patients, or a combination thereof.

In some embodiments, an outer surface of the inner sleeve (110) directly in contact with the bone cavity may be surface modified for osseointegration with the host tissue, anti-microbial property, load drugs, growth factors, peptides, small molecules to induce bone growth in diseased bone, osteoporotic, and geriatric patients, or a combination thereof. The apparatus (100) may further comprise sensors built into an outer surface of the inner sleeve (110), an outer surface of the outer sleeve (120), or a combination thereof to quantify the stress and motion between the inner sleeve (110) and the outer sleeve (120), the apparatus (100) and the bone. The apparatus (100) may further comprise one or more fixation provisions at at least one proximal end and at least one distal end of the inner sleeve (110) for securing the apparatus (100) to the surrounding bone.

In some embodiments, the present invention features an orthopedic intramedullary sleeve apparatus (100) for internal bone fixation for bone fracture treatment of a patient. The apparatus (100) may comprise a multilayer sleeve component comprising one or more access valves (130) disposed on a surface of the sleeve component. Each access valve may comprise one or more resealable ports for injecting a curable substance into the sleeve component. An access valve of the one or more access valves may comprise a first port to allow for injection of a curable material, and a second port to allow insertion of a light guide comprising a flexible plug configured to seal the light guide in the second port of the access valve.

In some embodiments, the sleeve component may comprise an inner sleeve (110) and an outer sleeve (120). The apparatus (100) may further comprise one or more sensors disposed on an outer surface of the outer sleeve (120), the inner sleeve (110), or a combination thereof. Each sensor of the one or more sensors may be capable of measuring pressure, stress, strain, temperature, or a combination thereof with respect to the sleeve component and the bone. In some embodiments, the sleeve component may be configured to conform to the intramedullary cavity and stretch to match growth of the bone. In some embodiments, the inner sleeve (110) and the outer sleeve (120) may be fabricated concurrently into a single sleeve with multi-functional features of inner and outer sleeve using a single manufacturing process. The single manufacturing process may comprise electrospinning.

The present invention features a method for applying an intramedullary sleeve apparatus (100) to a fractured bone to bond to the bone during bone fracture treatment. The method may comprise providing the intramedullary sleeve comprising, an inner non-resorbable intramedullary sleeve (110), having at least one proximal end and at least one distal end, and an outer intramedullary sleeve (120) disposed around the inner sleeve (110), having at least one proximal end and at least one distal end. The inner sleeve (110) and the outer sleeve (120) may be bonded together. The apparatus (100) may further comprise one or more access valves disposed through the inner sleeve (110) and the outer sleeve (120) so as to allow access into the inner sleeve (110). Each access valve may be disposed at at least one proximal end of the inner sleeve (110) and the outer sleeve (120), at least one distal end of the inner sleeve (110) and the outer sleeve (120), or a combination thereof. An access valve (130) of the one or more access valves may comprise a first port (132) to allow for injection of a curable material, and a second port (134) to allow insertion of a light guide (140). The apparatus (100) may comprise the light guide (140) disposed through the second port (134) of the access valve (130), the light guide (140) comprising a flexible plug (142) configured to seal the light guide (140) in the second port (134) of the access valve (130).

The method may further comprise creating one or more laparoscopy holes through a cortical layer of the bone at at least one distal end and at least one proximal end of the bone, applying one or more positioning guides to the intramedullary sleeve, positioning the one or more positioning guides between the one or more laparoscopy holes and through the bone, and applying, by the one or more positioning guides, the intramedullary sleeve within the bone.

In some embodiments, the method may further comprise steps for removing the intramedullary sleeve from the bone after removal of cured resin comprise inserting a mechanically operated tool having a hook in closed position through an access valve until it reaches an end of the sleeve, releasing the hook and engaging the sleeve through physical piercing, and pulling the tool out of the bone through the access valve. In some embodiments, the inner sleeve (110) and the outer sleeve (120) may be fabricated concurrently into a single sleeve with multi-functional features of inner and outer sleeve using electrospinning.

The present invention features an intramedullary sleeve apparatus (100) configured to hold and cure injectable bone cement, polymerized polymer, or a combination thereof to form an intramedullary device that conforms to the host tissue and supports a bone of a patient during bone fracture treatment. In some embodiments, the apparatus (100) may comprise an inner non-resorbable intramedullary sleeve (110), having at least one proximal end and at least one distal end. An interior of the inner sleeve (110) may comprise a reinforcing material (112). The apparatus (100) may further comprise an outer intramedullary sleeve (120) disposed around the inner sleeve (110), having at least one proximal end and at least one distal end. In some embodiments, the inner sleeve (110), the outer sleeve (120), or a combination thereof may comprise multiple prongs at the distal ends, proximal ends, or both, acting as multiple "ends" on the corresponding side. This is to accommodate bones having a non-straight shape (e.g. a Y-shaped bone).

The apparatus (100) may further comprise one or more access valves (130) disposed through the inner sleeve (110) and the outer sleeve (120) so as to allow access into the inner sleeve (110). Each access valve may be disposed at at least one proximal end of the inner sleeve (110) and the outer sleeve (120), at least one distal end of the inner sleeve (110) and the outer sleeve (120), or a combination thereof. An access valve (130) of the one or more access valves may comprise a first port (132) to allow for injection of a curable material, and a second port (134) to allow insertion of a light guide (140). The apparatus (100) may further comprise the light guide (140) disposed through the second port (134) of the access valve (130), the light guide (140) comprising a flexible plug (142) configured to seal the light guide (140) in the second port (134) of the access valve (130).

The apparatus (100) may further comprise one or more sensors disposed on an outer surface of the outer sleeve (120), the inner sleeve (110), or a combination thereof. Each sensor of the one or more sensors may be capable of measuring pressure, stress, strain, temperature, or a combination thereof with respect to the sleeve component and the bone. The inner sleeve (110) and the outer sleeve (120) may be fabricated by electrospinning. The inner sleeve (110), the outer sleeve (120), or a combination thereof may be configured to stretch to match growth of the bone. The apparatus (100) may be configured to be removed by external accessories. One or more properties of the inner sleeve (110) and the outer sleeve (120) may be determined based on a bone mass index of the patient. The sleeve component may be configured to conform to the intramedullary cavity and stretch to match growth of the bone.

In some embodiments, the reinforcing material (112) may comprise carbon fiber, Polyether ether ketone (PEEK), dense Polytetrafluoroethylene (PTFE), expanded PTFE, Polyethylene terephthalate (PET), titanium mesh, titanium-reinforced PTFE of a single material, polyether block amide, nylon, or a combination thereof. In some embodiments, the inner sleeve (110) may comprise one or more non-resorbable biocompatible materials comprising carbon fiber, polymer composites, non-resorbable materials such as dense PTFE, expanded PTFE, titanium mesh, and titanium-reinforced polytetrafluoroethylene of a single material, or a combination thereof. In some embodiments, the outer sleeve (120) may comprise one or more biocompatible materials comprising natural hydrogels, synthetic hydrogels, demineralized and decellularized bone, carbon fiber, polymer composites, bioceramics, bioactive glasses, glass-ceramics, polymer bioactive glass composites, poly(acrylonitrile), poly(6-aminocaproic acid), poly(decamethylene adipamide), Nylon 10,6, Poly(etheretherketone) (PEEK), Poly (ethylene terephthalate) (PET), poly(hexamethylene adipamide), Nylon 6,6, poly(hexamethylene suberamide), Nylon 6,8, poly(styrene), poly(4-methylpentene), high density polyethylene, ultra-high-molecular-weight polyethylene, polytetrafluoroethylene (PTFE), expanded PTFE, modified ethylene-vinyl acetate, modified polyester of homopolymer or co-polymers, block copolymers, or a combination thereof.

In some embodiments, the flexible plug (142) may comprise natural rubber, styrene butadiene rubber, butyl rubber, nitrile, neoprene, ethylene propylene diene monomer based rubber, silicone, fluoroelastomer (FKM), polyurethane based rubber, hydrogenated nitrile rubber, or a composition made with any of the above mentioned rubbers and thermoplastic or thermoset based materials. In some embodiments, the one or more access valves (130) may comprise silicone, silicone-based materials, synthetic or natural based elastomeric rubber materials, including natural rubber, styrene butadiene rubber, butyl rubber, nitrile, neoprene, ethylene propylene diene monomer based rubber, silicone, fluoroelastomer (FKM), polyurethane based rubber, hydrogenated nitrile rubber, or a composition made with any of the above mentioned rubbers and thermoplastic or thermoset based materials.

In some embodiments, the outer sleeve can be fabricated using 3D printing, braiding, knitting, weaving, electrospinning, injection molding, casting, extrusion, and welding, or any technology that can achieve the required physicochemical and mechanical properties. In some embodiments, the inner sleeve can be fabricated using 3D printing, electrospinning, injection molding, casting, extrusion, welding, or any technology that can achieve the required physicochemical and mechanical properties.

In some embodiments, the outer and inner sleeves can be surface modified: for osseointegration with the host tissue, anti-microbial property, load drugs, growth factors, peptides, and small molecules to induce bone growth in diseased bone of osteoporotic and geriatric patients. The surface modification can include plasma surface treatment, glow discharge method, chemical surface modification, coatings, radiation, lithography, including rough surfaces achieved by means of different fabrication techniques. The antimicrobial property of the sleeve can be achieved via direct surface modification by acids and alkali and incorporation of cationic groups such as quaternized ammonia or coatings of antimicrobial drugs such as gentamycin, tobramycin, antifungals like vancomycin to prevent post-operative infections.

In some embodiments, the multiport valve's first port may accept a diffusive light guide. The end that is outside the sleeve may be connected to light source. The light guide may be chopped right on the outside of the flexible plug after the curing process is complete.

In some embodiments, the multiport valve's second port from which polymer/resin/bone cement is injected inside sleeve may have an external 3-way stopcock attached to suck out all the air from sleeve creating a vacuum seal by turning the 3-way cock towards the syringe, and then injecting polymer/resin/bone cement. In other embodiments, this port may comprise a one-way valve, which is used to connect to the hose and syringe to inject polymer/resin/bone cement into the sleeves. This port may comprise flaps that open under pressure to allow material push inside. After injecting and if the injected material is under pressure, the flaps do not open to leak the material outside the sleeve, hence acting as a one-way valve. This is depicted in FIG. 14D.

The outer sleeve can have the following physical characteristics: sleeve thickness ranging from 50 µm to 1000 µm, pore size ranging from 10 µm surface pores to 1000 µm through pores, porosity ranging from 0% to 80%, porosity and pore size gradient in the mentioned ranges in either radial or longitudinal or both radial and longitudinal directions, different pore shapes such as circular, rectangular, pentagonal, hexagonal, octagonal, randomized, pores created by electrospinning, pores created by triply periodic minimal surface, or any pores that mimic the native bone architecture.

The inner sleeve can have the following physical characteristics: sleeve thickness ranging from 10 µm to 1000 µm, a leak-proof membrane that is non-porous (or) with porosity gradient from inner to outer wall wherein the outer wall is 100% dense, surface pores on the inside and outside walls but no presence of through pores. The inner sleeve can have the following mechanical characteristics: strain rate that can withstand the fracture and piercing of the bone cement, sufficient bond strength with bone cement to transfer the mechanical load from bone cement to sleeve to the surrounding bone. The inner sleeve can have an inside layer of a carbon fiber or carbon-based material, metal fiber or metal-based mesh, or glass fiber or glass-based mesh to improve the mechanical properties of the intramedullary device. This inside layer may be fused to the inside surface of the sleeve or may be a carbon fiber sleeve disposed inside the inner sleeve.

The inner sleeve can have sensors built into the outer surface of the inner sleeve to quantify the stress and motion between the inner and outer sleeve, and the intramedullary device and the bone. The intramedullary sleeve has fixation provisions at proximal and distal ends to attach external fixation devices such as screws to secure the in-situ cured intramedullary device. In some embodiments, these provisions are designed to exist only on the outer sleeve and in other embodiments, these provisions are designed to exist on the multi-layered sleeve system (both inner and outer laminated/bonded sleeve). In some embodiments, the provisions can also be positioned in the body of the sleeve system not necessarily only at the proximal or distal ends of the sleeve system.

The sleeve may be fabricated to match the overall three-dimensional shape of the bone cavity in any region of the skeletal system. The outer sleeve and inner sleeve of the intramedullary sleeve are either i) bonded only at proximal and distal ends (or) ii) bonded throughout their body length (or) iii) bonded at proximal and distal ends.

The outer sleeve can be fabricated having a designed porous structure that can expand radially when stretched in a longitudinal axis thereby growing surrounding the in-situ formed fixation device in the intramedullary canal allowing its application in pediatric populations with growing bones. The outer sleeve its physical properties including porosity, pore size, and mechanical properties may be designed and fabricated to that of patient's bone density and bone mechanical properties The inner sleeve may be made of a material such that it can withstand the heat released by cured bone cement or polymerization to protect the bone cavity. The inner sleeve may contain liquid monomer, polymerized polymer, unreacted monomer, if any, trapped in the polymerized polymer or bone cement from leaking into the bone cavity.

The inner sleeve can be surface modified to load antimicrobial drugs, bone morphogenetic proteins, or drugs to induce bone growth in diseased bone of osteoporotic and geriatric patients. The inner sleeve may have sufficient surface microporosity and physical and chemical properties that allow it to bond with the polymerized polymer or cured bone cement to an extent that such a bond can withstand the dynamic torsion, compression, tension, and bending loads applied on the in-situ formed bone fixation device.

The present invention features a method of creating a bone cavity in a bone that is suffered by a bone fracture or a disease that involves the creation of a hole or multiple holes drilled on the affected bone surrounding the fracture site or encompassing the entire diseased bone area wherein hole(s) are either created on both sides of the bone sagittal plane (or longitudinal axis or predominant bone axis) or on the same side of the bone sagittal plane (or longitudinal axis or predominant bone axis); followed by reaming of the interior of the affected bone using bone reamers that are accessed through the above-drilled hole(s) to create a bone cavity in the affected bone in such a fashion that the created bone cavity is interconnected with the hole or multiple holes created on the bone surface.

The drilled hole or multiple holes can have a diameter of 2 mm to up to 10 mm to create a less invasive surgical procedure. The affected bone can be any of the following: femur, tibia, fibula, tarsus bones, foot phalanges, metatarsal bones, radius, ulna, humerus, carpal, metacarpal, finger phalanges, hip bone, clavicle, scapula, vertebra, mandible, ankle, wrist, spinal articular surface bones including, but not limited to, the facet joint and the vertebral body, ribs, temporomandibular joint, pelvis, maxilla or any other bone that could allow the surgeon to access and create a hole and a cavity.

The intramedullary sleeve may be positioned in the cavity using an insertion device that is first inserted into the cavity through the distal end access valve and navigated through the cavity to the proximal end where the distal end of the sleeve is attached to the insertion device which is then pulled from the distal end valve of the bone to place in position. The intramedullary sleeve may be positioned in the cavity using a device that is first inserted into the cavity through the distal (or) farthest access valve amongst the multiple access valves that are created in the bone and navigated through the cavity to the proximal (or) nearest end, where the distal end of the sleeve is attached to the insertion device which is then pulled from the distal end valve of the bone to place in position.

The present invention features a method of removing the intramedullary sleeve system after bone fracture fixation or bone disease healing. A sleeve removal device may be used to remove the inner sleeve after the removal of bone cement; following which the sleeve removal process is a multi-step approach consisting of a detachment of the outer sleeve (if non-resorbed) from the inner sleeve and using a device that encompasses the open end of the inner sleeve accessed through the visible drilled hole during insertion procedure (access valve) post healing to remove the inner sleeve out from the bone cavity not allowing the leakage of remaining bone cement in the cavity. Removing the inner sleeve system that contains multiple access valves involves the removal of the associated nails (if used), closure of the access valve ends (if open), removal of branched divisions (in case of a complex 3D-shaped sleeve) first before removing the main body of the sleeve system.

The method may further comprise steps for removing the intramedullary sleeve from the bone after the removal of cured resin. In some embodiments, these steps may comprise inserting a catheter comprising one or more inflatable balloons through a resealable port and an access valve to an interior of the inner sleeve until the catheter reaches an end of the sleeve, inflating the one or more balloons to hold the inner sleeve, and pulling the catheter out of bone through the access valve. In some embodiments, these steps may comprise inserting a mechanically operated wire having a hook in a closed position through an access valve until it reaches the end of the sleeve, releasing the hook and engaging the sleeve through physical piercing, and pulling the wire out of the bone through the access valve. In some embodiments, these steps may comprise inserting a high vacuum tube through an access valve until it reaches the end of the sleeve, and actuating the high vacuum tube such that the sleeve is sucked out of bone through the access valve.

The aforementioned intramedullary sleeve may have one or more light guides capable of transmitting UV light. The light guide may be inside the inner sleeve and can be either wound on the surface or freely placed, and the light guide is either on the inside of the inner sleeve or outside of the inner sleeve wounded in different patterns. The entry of the light guide is either through the inside of the access valve of the sleeve or through the interface between the inner sleeve and access valve or through the interface between the inner sleeve and outer sleeve.

During the process of intramedullary reaming and sleeve insertion, bone fragments of fracture can be stabilized using bone glue, plates, and screws that are either made with biodegradable materials or non-biodegradable materials.

The aforementioned intramedullary sleeve system can be used to form intramedullary fixation devices for the following bone fractures, for example, chephalomedullary fixation, arthrodesis fixation, proximal humerus, and humerus fixation, tibia and femur fixations. To achieve the different bone fracture fixations, the aforementioned intramedullary sleeve system can be used in conjunction with the compatible and specifically designed plate and screw system taking the advantage of sleeve access valves as locations for screw fixation.

Traditional metallic implants do not grow with a pediatric patient's bone, during and after the surgical procedure and in almost all cases, the patient undergoes a revision surgery to replace the implant or follow-up surgery in recent state-of-the-art cases to extend the existing implant. the present invention's customized and patient-specific implant with auxetic design sleeve will provide an opportunity to allow the sleeve growth along with the bone as the outer sleeve has tissue in-growth and is in with apposition with bone endosteum while the cured polymer inside the sleeve remains at the same dimensions. This allows for more natural bone growth in and around the intramedullary device with marrow formation and sleeve expansion matching the patient's bone growth without undue pressure on the device or the bone tissue by the auxetic sleeve.

The core property of the auxetic sleeve design allows for a negative Poisson's ratio or a zero Poisson's ratio which would allow the material to either expand under elongation or remain the same diameter-wise. The auxetic-designed sleeves for pediatric applications will be 3D printed or designed and fabricated using traditional methods such as injection molding, etc, as required.

Electrospinning the nanofibers and the nano-to-micro range surface porosity that is achieved are useful for tissue in-growth, bonding, loading drugs, and being anti-microbial and anti-bacterial by avoiding biofilm formation and discouraging bacterial growth. In addition, drugs and osseointegrative proteins can be incorporated into the biopolymers that are electrospun. In some embodiments, the electrospun outer coating of the unisleeve is resorbable, but not the inner membrane. In some cases, the electrospun coating is non-resorbable.

In some cases, the fabrication of a three-dimensional unisleeve is obtained by first electrospinning a porous sheet of layered that is attached to a non-porous inner membrane followed by molding the composite unisleeve into a required 3D shape and attaching the necessary access valves and other accessories such as light guides, sensors, etc as required. In some embodiments, the non-porous inner sleeve layer is first fabricated into the required 3D shape and is positioned on the spinning mandrel, which is followed by electrospinning the required polymer solution onto the spinning mandrel and on top of the 3D shape to obtain a unisleeve.

The Sleeve System: The main components and their properties are briefly described below. FIG. 2 illustrates one type of typical IM sleeve configuration.

Internal Sleeve: The functions of the internal sleeve are to contain the photocurable resin or monomer or polymer immediately after injection into it, conform to the bone cavity, withstand the heat released during the polymerization process, bond with the polymer after polymerization, and maintain its structural integrity and physical characteristics after polymerization for a short or long-term until the fracture healing, doesn't degrade with the exposure to light during the polymerization, doesn't degrade during the heat and energy applied or released during the removal of the cured resin or cement. Some materials that fit such properties are dense PTFE, expanded PTFE, PEEK, carbon-reinforced PEEK, high-density polyethylene, titanium mesh, and titanium-reinforced polytetrafluoroethylene of a single material, PETG, carbon, cellulose, PET, ethylene vinyl acetate (EVA), poly(acrylonitrile), poly(6-aminocaproic acid), poly(decamethylene adipamide), Nylon, Poly(etheretherketone) (PEEK), Poly(ethylene terephthalate) (PET), Polyurethane, PEBAX, poly(hexamethylene adipamide), poly(hexamethylene suberamide), poly(styrene), poly(4-methylpentene), high density polyethylene, ultra-high-molecular-weight polyethylene (UHMWPE), polytetrafluoroethylene (PTFE), expanded PTFE, ethylene-vinyl acetate (EVA), modified EVA, polyvinylidene fluoride (PVDF), polyvinyl chloride (PVC), modified polyester of homopolymer or co-polymers, block copolymers, or a combination thereof. In some embodiments, the internal sleeve might need to function only some of the above-listed functions and can be made with a different material.

For example, in some situations, there is no need for device removal and therefore the selection of internal sleeves in the sleeve system can be completely different. For the sleeve to satisfy those functions, sleeve materials are engineered to provide the appropriate functions. In some embodiments, the outer surface of the internal sleeve is surface modified to load the antimicrobial drugs, therapeutic drugs, and osteostimulative proteins for safe and efficient treatment. In some embodiments, the inner lining of the internal sleeve will have a roughened surface with nano to micro-sized surface pores, will have a textured surface, or will have nano- to micro-sized bristles for effective bonding with the injected and polymerized polymer. In some embodiments, the inner surface of the internal sleeve will have aligned or randomly oriented carbon fibers or the entire thickness of the sleeve will be a radial gradient composite with 50% carbon fibers on the inner surface and 0% carbon fibers on the outer surface. In some embodiments, braided or woven carbon fibers will be lined inside the internal sleeve forming an additional layer. In some embodiments, the continuous carbon fibers are glued to the sleeve and in some embodiments, the carbon fibers are only glued at the ends while the longitudinal body is free floating inside the internal sleeve.

Figure 3:
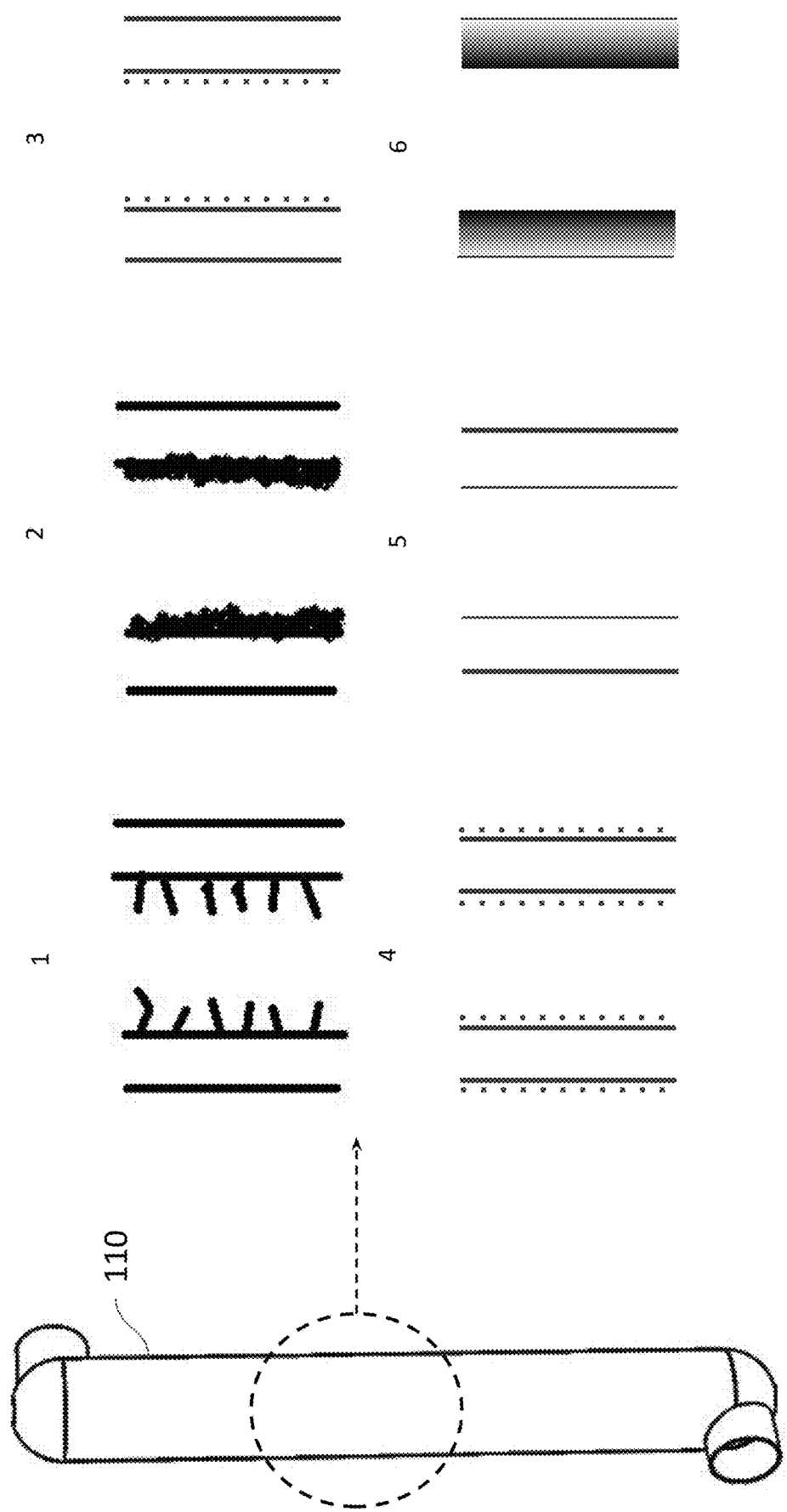
Figure 6A:
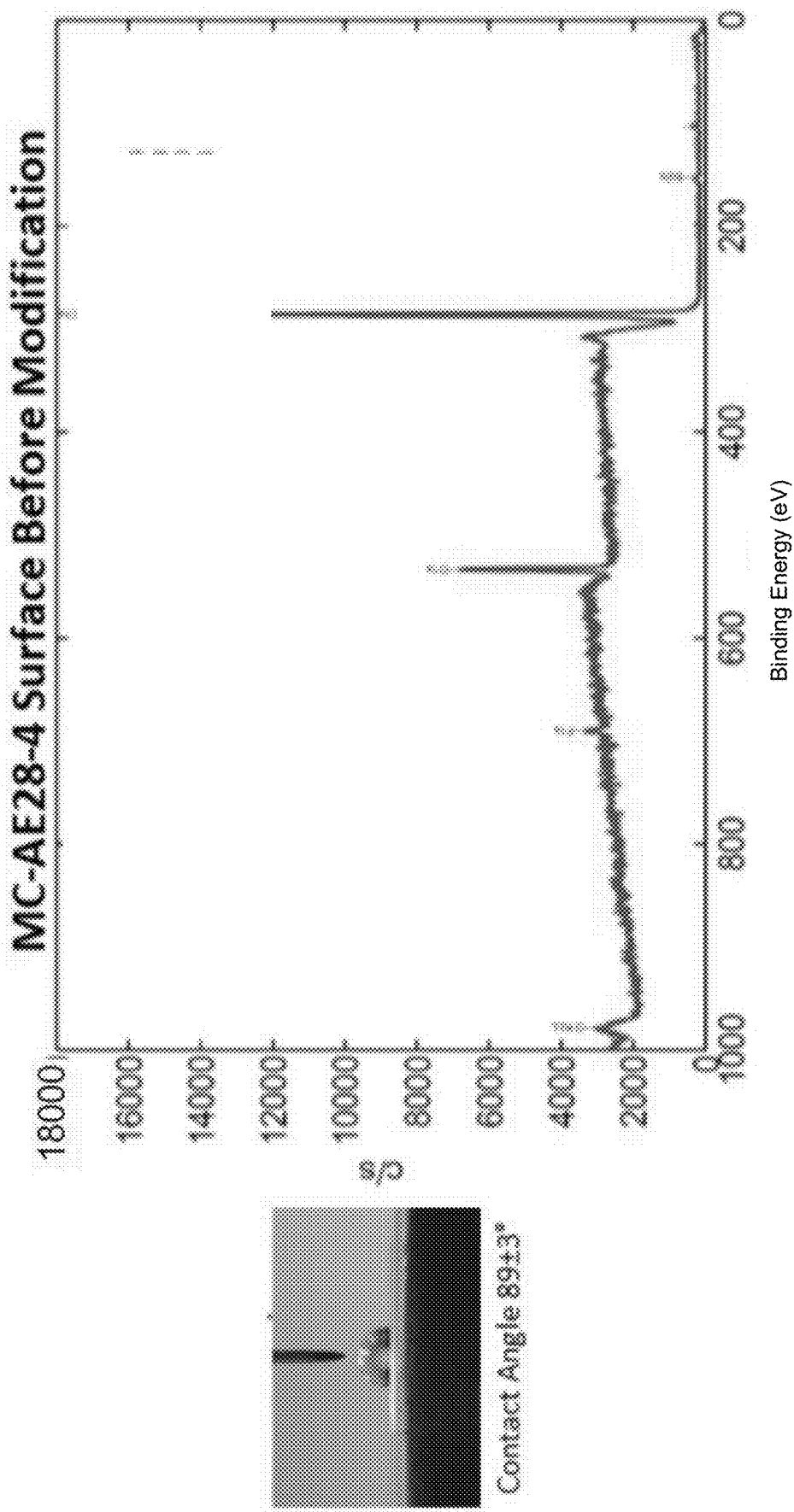
Figure 6B:
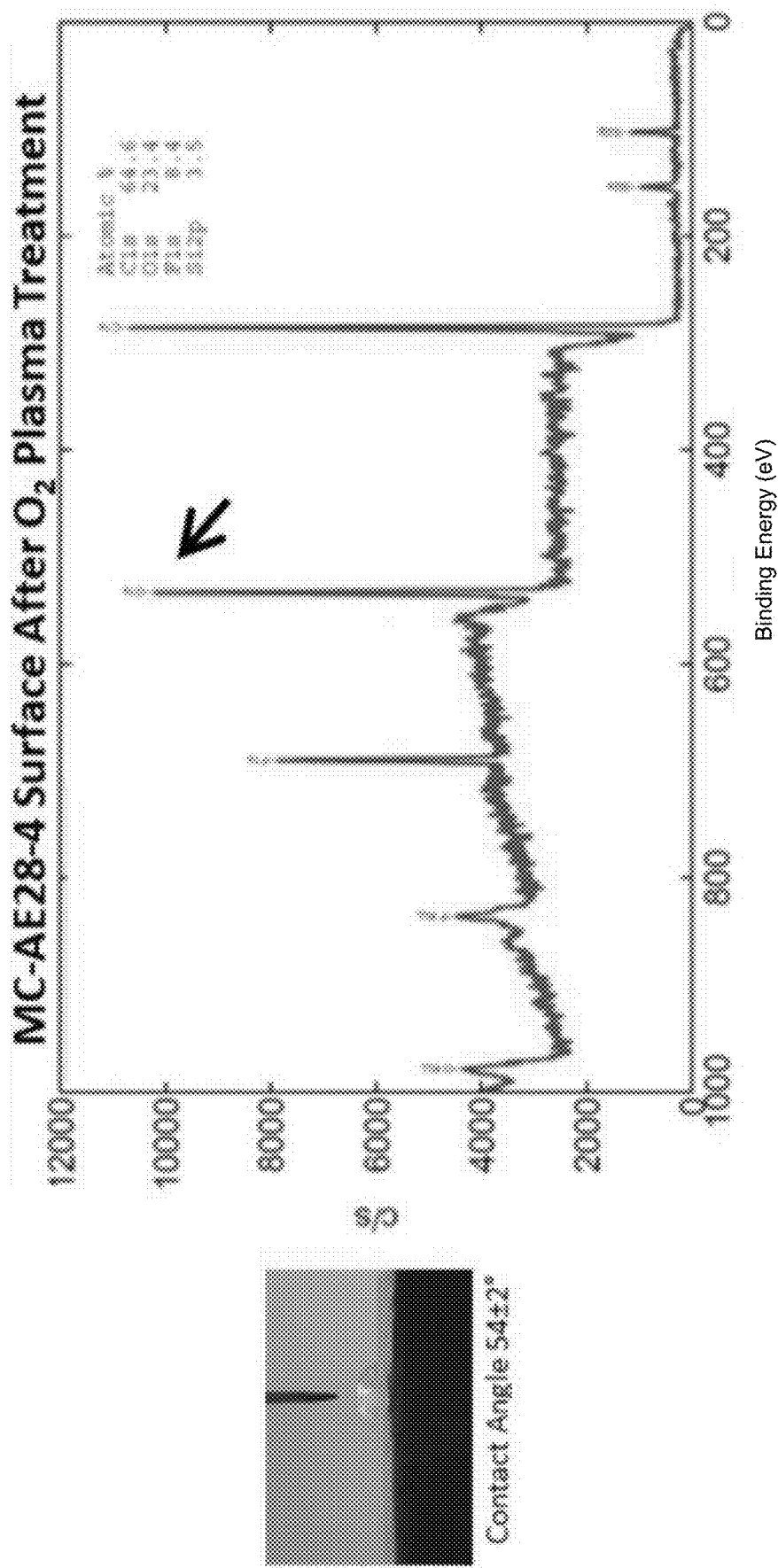
Figure 6C:
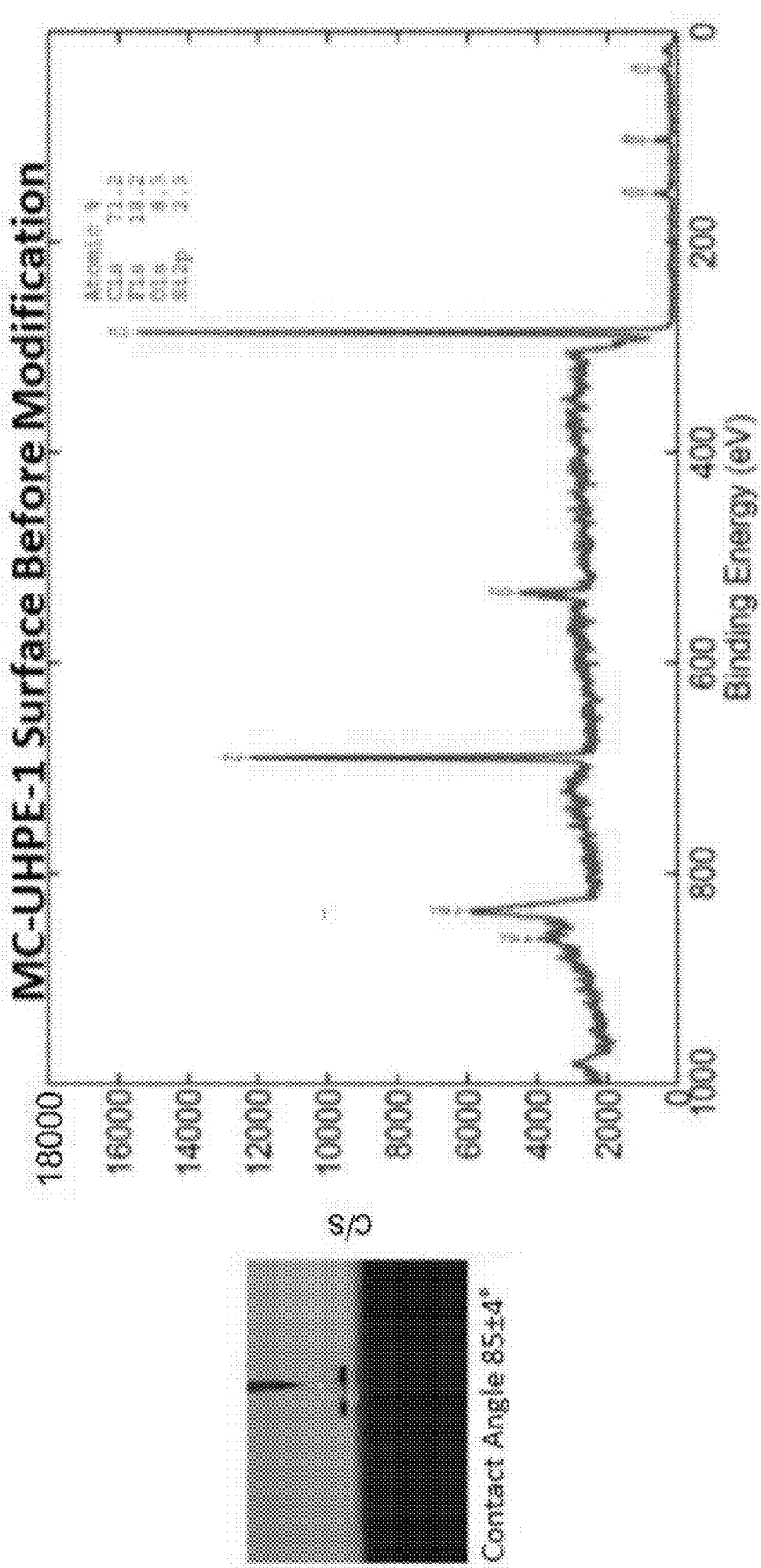
Figure 6D:
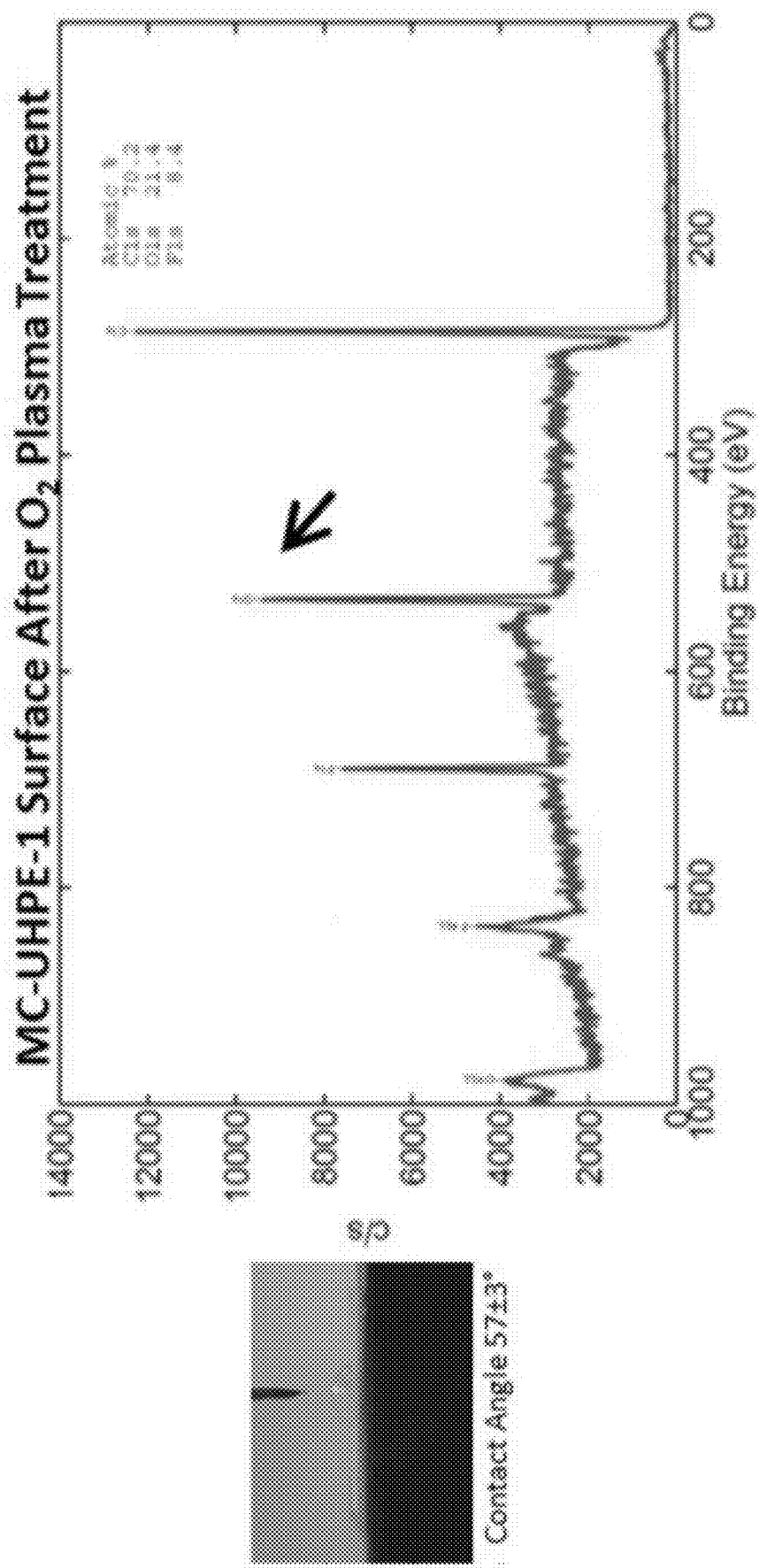

FIG. 3 illustrates the internal sleeve design with some of the above-mentioned embodiments. In some embodiments, the light energy source in the form of light guide wires will be a part of the inner surface of the sleeve or the outer surface of the sleeve. The said light energy source could be a single guide wire or a series of wires oriented either parallel or wrapped in a helical structure or any other structure on the inside or outside of the internal sleeve. In some embodiments, there can be implantable electronic sensors not limited to pressure sensors, temperature sensors, and strain gauges attached to the internal sleeve. These sensors would provide the continuous monitoring of expansion and pressure inside the internal sleeve immediately after filling the sleeve with a biocompatible polymer or photocurable resin system or monomer or commercially existing bone cement system. The sensors could also provide the details of temperature, strain, and pressure.

External Sleeve: The primary function of the external sleeve is to conform to the bone cavity and stay pressfit to the endosteum or the cavity surface, allow osseointegration with the surrounding bone tissue and offer the first defense of protection to the internal sleeve from the rough bony environment immediately after the fracture. After the injection of the biocompatible polymer into the internal sleeve, the expanded internal sleeve will push the external sleeve to align with the bone endosteum. To enable this, the external sleeve should have physical properties that match the surrounding bone tissue in terms of surface properties, porosity, pore shape, and physical, biological, and mechanical properties. The external sleeve will be made with either a non-degrading or a degrading biocompatible polymer that has comparable mechanical properties to that of the surrounding bone tissue.

The non-degrading materials for the external sleeve could be based on carbon, PEEK, natural hydrogels, synthetic hydrogels, demineralized and decellularized bone, carbon fiber, polymer composites, bioceramics, bioactive glasses, glass-ceramics, polymer bioactive glass composites, poly (acrylonitrile), poly(6-aminocaproic acid), poly(decamethylene adipamide), Nylon 10,6, Poly(etheretherketone), Poly (ethylene terephthalate), poly(ethylene terephthlate) (PET), poly(hexamethylene adipamide), Nylon 6,6, poly(hexamethylene suberamide), Nylon 6,8, poly(styrene), poly(4-methylpentene), high-density polyethylene, ultra-high-molecular-weight polyethylene, polytetrafluoroethylene PTFE, Dyneema fibers, cellulose-based materials, expanded PTFE, modified ethylene-vinyl acetate, modified polyester of homopolymer or co-polymers, block copolymers or a combination thereof that can be made into a porous sleeve. The degrading materials for the external sleeve could be bioresorbable polymers that are either synthetically made or naturally derived polymers, hydrogels, hydroxyapatite, resorbable bioactive glasses, glass ceramics, extracellular matrix powders, demineralized decellularized bone tissue or similar materials that can either resorbed by the body or eventually become part of the bone.

In some embodiments, the external sleeve is fabricated on top of the inner 3D sleeve during the fabrication process to achieve a unified intramedullary sleeve body but has two different microstructures. An example of the above system could be an electrospinning setup wherein a conductive internal sleeve would not only act as a substrate for depositing the fine microfibers for the external sleeve but also act as a 3D shape that allows the in-process bonding of internal and external sleeves. In some embodiments, the internal sleeve itself could suffice to act as an external sleeve. In some embodiments, the external sleeve is bonded in its entirety to the internal sleeve or bonded only at the distal and proximal ends or bonded together with sleeve ends at the access valve junction that contains a valve for polymer injection and light guide attachment. In some embodiments, the external sleeve is 3D printed to achieve the properties of an auxetic mesh tube that when extended in a longitudinal direction will maintain or even expand in radial dimensions without exerting excessive radial pressure on the endosteum. In some embodiments, the external sleeve will be able to elongate itself longitudinally to match the growing bone without undergoing any radially compressive behavior.

The external sleeve would have porosities ranging from 5% to 70% and pores ranging from 10 μm to 300 μm or even up to 800 μm to match different regions of the bone. In some embodiments, the external sleeve could have only surface porosity and not see-through porosity. The required porosities or pore sizes will be achieved by controlling the fabrication parameters using a variety of fabrication techniques including braiding, knitting, weaving, electrospinning, 3D printing, or similar fabrication techniques that could achieve the result. FIGS. 4A-4H shows some examples of such braided, woven, and 3D-printed meshes. In some embodiments, sensors can be embedded into the external sleeve during its fabrication process, or an external sensor can be stitched or attached to the external sleeve as required. In addition to providing the details such as temperature, strain, and pressure, sensors could also be used to detect the micromotion between the external and internal sleeves which could be an indirect indication of the fit and integration of the in-situ formed IM device in the intramedullary cavity or bone cavity.

Uni-Sleeve: Uni-sleeve is another innovative and alternative way of replacing the need of having both internal and external sleeves. Uni-sleeve serves all the primary functions of both the external and internal sleeves mentioned above. Uni-sleeve is a singular sleeve system that has one or more openings as required to fit the method of bone fracture treatment. Uni-sleeve will contain necessary accessories at the above-said opening(s) to control the flow of liquid polymer, monomer, photocurable resin system, or any other photocurable or commercially existing acrylic-based cement system. The accessories at the above openings will also allow light guides, light sources, electronic accessories, attachments, and sensors inside the Uni-sleeve. It is essential for Uni-sleeve to have an internal rough or sticky surface for the polymer penetration and to have a good bonding with the polymer; and, an external porous architecture to bond with bone endosteum and have a good bone in-growth. Typically, porous architecture for bone in-growth would be pores in the range of 100-300 μm or even 800 μm depending on the bone region.

In some cases, the Uni-sleeve's external porous architecture could be a coating of bioresorbable materials or surface modification, or coating of osteo-stimulatory proteins to improve tissue integration. In some cases, the external porous architecture could be made with a composite of bioresorbable polymer and demineralized bone matrix or a demineralized bone matrix. The primary function of the coating is to bond with the surrounding bone tissue and to offer the first defense of protection to the internal surface of the Uni-sleeve from the rough bony environment. In some embodiments, Uni-sleeve is a lamination of both internal and external sleeves that acts as a singular structure in terms of its flexibility and function. Such a lamination can be achieved using heat or biocompatible glues such as catechol functionalized styrene or others and any other commercially existing ones such as silicone or acrylate-based adhesives rated for long-term implantation. In some embodiments, Uni-sleeve fabric is 3D printed using a 3D printer capable of multi-material extrusion, and later the fabric is molded to the required shape.

In some embodiments, the 3D Uni-sleeve is directly printed to its shape. In some embodiments, the Uni-sleeve is assembled through a series of fabrics that could function as external coating and internal coating but the Uni-sleeve itself acts as a singular unit. In some embodiments, Uni-sleeve is fabricated using the electrospinning process. In this electrospinning process, the rotating mandrel is shaped in the form of a required mold of the bone cavity with necessary tolerances and is covered with an internal layer of the Uni-sleeve which also acts as a conductive sheet and a collective electrode. During the spinning process, the external coating material of the Uni-sleeve is spun on the spinning 3D-shaped collector by adjusting the voltage, distance, extrusion sir pressure, tip, and all other necessary parameters to form the required coating at a required porosity and pore shape.

After finishing the spinning process, the entire 3D shape is removed and a Uni-sleeve with an internal layer and external coating is achieved. The entire Uni-sleeve is then assembled with required access valves and is sterilized for use. In some embodiments of the Uni-sleeve, electronic sensors can be attached to the inner or outer surface of the Uni-sleeve as required to obtain the necessary conditions of the implant-bone interface and the implant condition.

Preliminary Results: Mechanical properties of potential sleeve membranes. A crucial requirement for the IM sleeve is to sustain the expansion under pressure during bone cement injection. Shortlisted candidate materials were selected based on the existing FDA-approved materials that are suitable for long-term implantable and have maximum potential in terms of elasticity, heat insulation, bonding with injected bone cement, its ability to act as a barrier to the body fluid, and prevent leakage of unreacted monomer into the bone cavity.

In addition, other crucial aspects include the processability of the material to be molded into desired bone cavity shapes. Some of the membranes with their properties are listed in Table 1. The preliminary testing of candidate membranes in terms of their elasticity, heat insulation, and bonding with bone cement showed positive results. It must be noted that the actual strength and stiffness of potential internal sleeve membranes are relatively low and cannot be a major deciding factor because injected biocompatible polymer (in this example, acrylic bone cement) would eventually provide the required stiffness to the intramedullary rod. FIG. 5 shows some of the summarized physical properties of candidate polymer membranes for the internal sleeve.

Surface modification of candidate membranes. Bonding of acrylic resin to sleeve membrane is important in the development of injectable strategy as the bond needs to withstand the tensile, compressive, bending, and torsional forces. Some of the FDA-approved and commercially available implantable grade membranes were tested for their bonding ability with acrylic resins. While materials such as ultra-high molecular weight polyethylene showed poor bonding, ethyl vinyl acetate, polyurethanes, and expanded polytetrafluoroethylene showed varying degrees of bonding depending on their specific composition.

To improve the bonding of the membranes, it was hypothesized that surface modification of membranes using a low-energy plasma would create nano to micro-sized imperfections on membrane surfaces with the hydrogen atom removal and formation of active carboxyl groups that would improve the bonding with injectable bone cement. For example, FIGS. 6A-6D show the improvement in the water contact angle of EVA and UHMWPE membranes after oxygen plasma treatment. The right panels of FIGS. 6A-6D clearly demonstrate the peel testing result of the EVA sample. After surface modification, the bond was so strong that EVA expanded to the extension limit of the testing machine without breaking the membrane. Some additional peel test specimens are shown in FIGS. 7A-7B.

Curing and bonding of acrylic cement to sleeve. The curing and bonding of acrylic cement are important characteristics in developing an injectable strategy and for the synchronous function of the intramedullary device with the IM sleeve system. Optimized time for cement curing or photocurable resin curing or biocompatible polymer setting inside the IM sleeve should provide a balance between providing the orthopedic surgeon sufficient time to plan for the surgical procedure and for a fast setting for quick patient recovery and reduced surgical time. Although curing time is not a subject of this work, peel test specimens were fabricated to investigate the bonding between cured cement and internal IM sleeve membrane based on the ASTM D903 standard. Results indicated that polycarbonate-based polyurethanes, ethylene vinyl acetate, and expanded polytetrafluoroethylene membranes show good bonding with acrylic resin.

Briefly, 1 cc of cement was injected and cured in hollow inner sleeves measuring 5 mm in diameter and 50 mm long made with candidate materials as listed in FIG. 5 and the samples are shown in FIGS. 7C-7E. FIG. 7E shows fractured test pins clearly demonstrating that inner membranes hold up to the tensile and compressive forces and contain acrylic resin. Moreover, measured properties all lie in the range for human bone. In addition to testing using small pins, structural properties were also evaluated by filling the cavity of hollow resin tubes (commercially available synthetic Sawbones®; measuring 10 mm in diameter, 150 mm long, 6 mm cavity) after allowing the acrylic resin to cure in the cavity with and without sleeve materials. These coupons were tested in a four-point bend fixture based on the ASTM F1264 standard (recommended for IM rods). A more than 100% increase in the strength of the Sawbone® tube was all values recorded were in the range for load-bearing bone. Overall, preliminary mechanical test results show the potential of candidate membrane materials together with the acrylic resin to satisfy the structural requirements of the intramedullary device or rod for human bone.

In vitro degradation and cytotoxicity of the polymers, Polymeric membranes mentioned in FIG. 5 were incubated in sterile deionized (DI) water, phosphate-buffered saline (PBS), and collagenase-loaded minimum essentials medium (MEM) with zinc from 48 hours to up to 14 days at 37° C. to study the material stability and degradation products (if any). The incubated polymeric membrane was analyzed for mass loss and chemical changes by FT-IR. Media collected after incubation was analyzed for polymer degradation products by FT-IR and MTT assay was performed to determine in vitro cytotoxicity using human mesenchymal stem cells. The polymeric membrane was very stable even after 14 days of incubation in PBS and did not show any significant mass loss or structural or chemical changes. The liquid collected after 24 hrs, 7 days, and 14 days were incubated with human mesenchymal stem cells for 24 hrs, and the MTT assay did not show any adverse cytotoxicity, and more than 90% cell viability was observed.

Figures 8A, 8B:
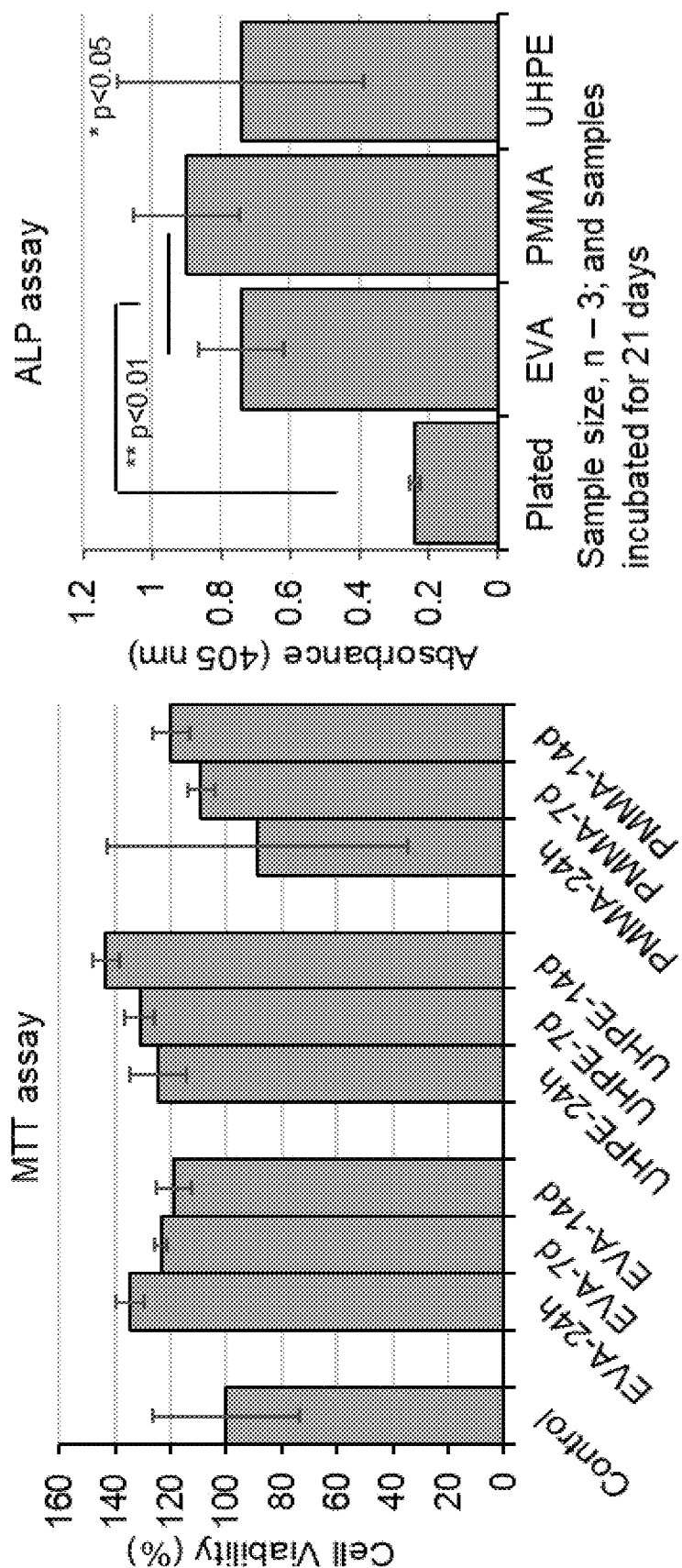
FIG. 8A shows cell viability in extractables from samples incubated in Dulbecco's Modified Eagle Medium (DMEM) and collagenase for 24 hrs, 7 days, and 14 days.
FIG. 8B shows an ALP activity assay using a p-Nitrophenyl Phosphate (pNPP) method.

Preliminary results indicated no cytotoxicity on human mesenchymal stem cells (hMSCs) when co-cultured with extractables of EVA, UHMWPE, and PMMA as shown in FIGS. 8A-8B. The samples were conditioned in Dulbecco's Modified Eagle's Medium (DMEM) with added Collagenase from *Clostridium histolyticum*. There was no statistically significant difference among groups and between groups. An osteogenic differentiation assay was also performed on sleeve membranes and PMMA discs using MG63 cells (osteosarcoma cell line that is arrested in a pre-osteoblast state). Cells were incubated with materials for 21 days and an alkaline phosphatase (ALP) activity assay using the p-nitrophenyl phosphate (pNPP) method was performed following manufacturer protocol. The pNPP activity indicated potential cell differentiation and the potential of membranes to bond with the bone and allow the mesenchymal stem cell population in the endosteum region to adhere, proliferate and differentiate to bone thereby allowing a good tissue integration with the sleeve and IM device.

Insertion Strategies: Intramedullary fixation is the standard treatment for diaphyseal fracture of the femur, tibia, humerus, radius, and ulna. Intramedullary nailing is performed via an antegrade or retrograde route through minimal soft tissue exposure. The Antegrade and retrograde nailing route is used for both femoral and humeral bones whereas, the retrograde route is used for the tibia and radius and antegrade for the ulna. Extensive reaming of the medullary canal is required to insert the intramedullary nail which may result in loss of blood supply to the cortical bone, increased risk of infection, risk of pulmonary embolism, and not advised for open fractures. Conventional intramedullary nails or rods are designed differently, and the majority of the nails are cannulated to be internally placed using a guide wire. These rods often require proximal and distal interlocking screws to stabilize the fractured bone as they have no control over the rotation and compressive forces.

The present intramedullary sleeve is designed to overcome these limitations or challenges posed by conventional intramedullary nails or rods. The present intramedullary Sleeve consists of either a multi-layered sleeve system or a Uni-sleeve or any customized sleeve system as determined by the physician, or a software program aiding the physician's decision customized to the patient's requirement. The present intramedullary sleeve can be implanted via antegrade, retrograde, or any route using a minimally invasive surgical technique. It can be placed within the medullary canal using a guide wire with minimal intramedullary reaming. In some embodiments, the cavity is reamed, and keyholes are made on either side of the fracture location, proximal and distal, through the cortex through the medullary cavity. A special guide wire with one end having a crochet hook and latch is then inserted through the proximal keyhole, and through the medullary cavity and fracture area until the hook is accessible through the distal keyhole. The above procedure performed will enable fracture reduction.

Following this, the IM sleeve is hooked to the guidewire at the distal keyhole and pulled to set in place until the drawn end of the sleeve with the access valve sits on the bone periosteum through the proximal keyhole. Later, biocompatible polymer or resin is injected through the access valve into the IM sleeve and cured thereby providing the intramedullary fixation of the fracture. In some scenarios, the insertion of the IM sleeve is flipped meaning the guide wire is inserted through the distal keyhole, and the IM sleeve is latched to the guide wire at the proximal keyhole and pulled to set in place until the drawn end of the sleeve with access valve sits on the bone periosteum through the distal keyhole. In some embodiments, the IM sleeve is set in place through only one keyhole. In such scenarios, one guide wire is first inserted into the medullary cavity and through the fractured area until the reamed end is reached.

Upon reduction, the fractured pieces are held in place, and a second guide wire with the special crochet hook and latch is attached to one end of the IM sleeve and the sleeve is inserted into the medullary cavity until the end is reached. Then, the IM sleeve is unlatched, and the special guide wire is removed immediately followed by the removal of the first guide wire. In some embodiments, the IM sleeve system is kept in a flexible tube and the tube is inserted through the keyhole to transfer the sleeve into the bone cavity and to set in position following which the flexible tube is retracted back. In some embodiments, the IM sleeve can be set in the cavity using an inflatable catheter. In this scenario, the inflatable catheter is first inserted into the IM sleeve followed by insertion into the proximal or distal keyhole and positioning of the IM sleeve between keyholes and around the fractured area.

Following this, the balloon on the catheter is inflated to push the IM sleeve so that it is in apposition with the endosteum. Finally, the balloon on the catheter is deflated and the catheter is removed from the IM sleeve. In some embodiments, the length of the inflatable balloon on the catheter is the same as the IM sleeve length. In some embodiments, there can be one or more smaller inflatable balloons throughout the length of the catheter between the keyholes.

In some embodiments, the one or more positioning guides may comprise guide wires disposed on the surface of the intramedullary sleeve, inflatable catheters disposed within the intramedullary sleeve, or a combination thereof. The method may further comprise removing the one or more positioning guides from the bone, leaving the intramedullary sleeve in place. The bone cement may be injected or otherwise applied to the sleeve after the guide wires are removed.

The guide wires used to position the IM sleeve system could be typical orthopedic guide wires such as the thinner version of Kirschner wire or a conventional orthopedic guide wires used to fix the tibia or any such appropriate guide wires can be used to fix the two broken pieces in case the bone is fractured into distinct pieces. In such scenarios, if the guide wire is unable to be guided through the two fractured pieces, another guide wire, K-wire or an aiming device can be used using the secondary access hole to align the bones. Once the bones are aligned, the guide wire is positioned in place. A flexible intramedullary reamer can be used to minimally ream the bone as required but might not be always necessary for use with the IM sleeve system.

Following this, the IM sleeve positioning guide wire is slid over the previously placed guide wire with the help of certain provisions such as hooks, cavities, rings, etc into the bone cavity or intramedullary cavity. This IM sleeve positioning guide wire not only holds the IM sleeve but also transfers the sleeve inside the intramedullary cavity and positions it in place. This IM sleeve positioning guide wire can be a flexible tube with attached hooks, coil-like or spring-like structures where the IM sleeve is positioned inside the tube or spring or coil channel. In some scenarios, the IM sleeve positioning guide wire is a flexible tube-like or porous tube-like structure that can hold the IM sleeve inside the tube and has external sliding provisions such as hooks, cavities, rings, etc to enable gliding over the previously positioned guide wire.

The access valves are an important part of the IM sleeve system that could play the role in inserting, positioning, polymer injection, and removal of the sleeve system. To enable appropriate insertion and positioning, the IM sleeve access valve could sometimes contain a dedicated opening or port to allow the insertion and removal of the aforementioned catheter setup and accessories. In some embodiments, the IM sleeve access valve contains an opening that allows one-way injection of the biocompatible polymer or resin into the sleeve. In some embodiments, the access valve contains a dedicated secondary opening or port that is self-closing to allow an external optical guide wire to carry the light source or any other alternative energy source to cure the polymer or to remove the cured polymer. In some embodiments, the proximal (or distal) access valve of the IM sleeve has only one opening to allow the one-way injection of the biocompatible polymer or resin and the distal (or proximal) access valve of the IM sleeve has one opening or port to allow optical guide wire.

In some embodiments, both access valves of the IM sleeve have one or more resealable openings or ports—one to inject biocompatible polymer and the other to allow an optical guide for transmitting light energy or other external energy or catheter. In some embodiments, the IM sleeve is in a three-dimensional shape that fits the appropriate fracture treatment region. In some cases, the 3D IM sleeve can take the shape to fit the region between the femoral shaft and the femoral head through the intertrochanteric regions to enable fracture fixation of femoral neck fracture and intertrochanteric region fracture. The IM sleeves for such intensive fracture fixation are specially customized with high-strength medical-grade carbon fiber linings and materials that withstand complex and high load profiles. FIG. 9A-9G and FIGS. 10A-10F represent a couple of examples of many ways of inserting the IM sleeve.

The three-dimensional intramedullary sleeve offers flexibility to accommodate different regions in long bones and different kinds of fractures in long bones, will not cause infection unlike the cannulated IM rods, and upon filling the sleeve with biocompatible polymer or resin, it takes the shape of the medullary cavity providing a natural conformal contour locking and the sleeve osseointegrates with the host tissue. In addition, as required in certain situations, the sleeve system can also be locked with interlocking screws in the provisions that are specially made on the IM sleeve system to help prevent torsional forces. In some situations, the interlocking screws can also be drilled into the IM sleeve system at any location as desired by the physician after the curing of injected polymer.

Customized Non-Return and Removable Valve Mechanism: The IM sleeve system is designed to briefly receive and hold the injectable biocompatible polymer, resin, or even a polymer or a monomer in liquid or semi-viscous or viscous form until it is polymerized. After polymerization, the IM sleeve permanently protects the polymer from tissue infiltration. Therefore, it is of utmost importance that the IM sleeve system won't leak the non-solid injection of polymer or resin, or monomer during the process of injection and polymerization. In addition, the IM sleeve is designed to be removed in a minimally invasive or less invasive fashion on-demand after the fracture treatment or for any other reason.

The sleeve removal in such a fashion requires the removal of cured polymer inside the IM sleeve. To enable both above scenarios, the IM sleeve is designed with access valve(s) at the end(s) of the sleeve that aligns with the keyhole(s). These access valves are made with a valve opening mechanism that is based on the antegrade or retrograde flow of injectable biocompatible polymers. Each access valve of the sleeve contains one or more valves that are oriented to provide access to the interior of the sleeve's main body for injecting, inserting tools and(or) optical wires for polymerization, and inserting tools and(or) wires for removal of cured polymer.

The access valves are custom-built with materials that are compatible with the injected polymers, resins, or monomers. The valves and the valve mechanisms in the valves do not react with the injectable materials and are at the same time compatible and resistant to the external guide wires, optical cables, and other tools that are inserted into the valves as required during the sleeve removal process. The valve(s) of each access valve is designed to accomplish: i) control the biocompatible polymer or resin or monomer injection, ii) withstand the pressurized injection, iii) allow external or internal aids such as optical light guide, guide wires, tubes, etc as required for polymerization to pass through the access valve, iii) do not allow or limit the number of physiological fluids that comes into contact with the cured polymer and penetrate the inside of sleeves, iv) allow the external tools, light guides, ultrasonic tools, tubes, etc to easily penetrate during the cured polymer removal and sleeve removal process.

FIGS. 11A-11D show a couple of different mechanisms—duckbill valve and silicone diaphragm valve type mechanisms. In the duckbill mechanism, the external tools are easily accessed through the manipulation of the duckbill flaps whereas, in a diaphragm style valve mechanism, the rigid supports are interventionally removed using external heat/ultrasonic/any other energy sources to provide access to the polymer material and sleeves. Therefore, it is of utmost importance that the access valves and valve mechanisms are fabricated with materials that provide good surface characteristics to enable the smooth flow of polymer or resin, or monomer and provide excellent thermal stability.

Some materials could be silicone, silicone-based materials, synthetic or natural based elastomeric rubber materials including natural rubber, styrene butadiene rubber, butyl rubber, nitrile, neoprene, ethylene propylene diene monomer based rubber, silicone, fluoroelastomer (FKM), polyurethane based rubber, hydrogenated nitrile rubber, or a composition made with any of the above mentioned rubbers and thermoplastic or thermoset based materials.

In some embodiments, the access valves are bonded and part of the IM sleeve system. In some embodiments, access valves are fabricated separately and bonded or affixed at a later stage to form an integrated sleeve system. In some embodiments, the IM sleeve system kit will contain different access valves with one valve, two valves, or customized openings to fit the surgical procedure. In such scenarios, the physician will have the control to choose an appropriate access valve for the sleeve to deliver the bone cement or remove the bone cement. In some embodiments, these access valves are affixed by screwing to the sleeve system. In some embodiments, access valves are press fitted to the sleeve system. In some embodiments, access valves are affixed to the sleeve end in a barbed-style fitting. In some embodiments, the access valve will be a simple one-way valve. In some embodiments, the access valve is heavily customized with multiple resealable ports to cater to the needs of the surgical procedure. In some scenarios, access valves are only required during the insertion and curing stage and are immediately removed after curing the polymer and setting the fracture. In some scenarios, access valves are left inside the patient's body on the bone periosteum permanently until the sleeve must be removed.

Provisions for Enabling Polymer Curing: IM sleeve system is designed to accept biocompatible polymers, monomers, resins, etc that are curable using different polymerization mechanisms including free-radical polymerization and photopolymerization, and any other curable and settable polymers. In order to satisfy the specific curing requirements and characteristics of the polymer or resin or monomer being injected, the IM sleeve is designed to withstand and be compatible with these requirements. Some of these requirements include i) protecting the high heat released during any exothermic reactions into the medullary cavity, ii) bonding with the injected and cured polymer, iii) the ability to shield any external light energy source from not penetrating through the sleeve and into the medullary cavity or bone cavity where the sleeve is placed, and iv) ability to shield the heat released from polymer spilling into the bone cavity or medullary cavity during the polymer removal through any external energy means, and finally.

In addition, IM sleeves also have additional requirements such as providing radiopacity when injected with in-situ curable polymer with or without radiopaque additives. In some embodiments, IM sleeves will be fabricated with radiopaque additives. In some embodiments, IM sleeves will have radiopaque markings that makes the device visible under radiation. Most of the above requirements are satisfied by choosing different candidate materials for the sleeve system. All sleeve materials have a melting point that is higher than the curing temperature. For example, in a scenario where a large-sized sleeve is inserted into a large bone defect encompassing the entirety of the medullary cavity such as a femur, it can take a relatively high volume of a biocompatible polymer and the amount of heat released during polymerization (either free-radical or photopolymerizable) is significant. A multi-layered sleeve system and choosing a carbon fiber sleeve not only reduces the heat being released to the medullary cavity but also shields the surrounding tissue from heat and unwanted light exposure.

IM sleeve systems designed for photocurable biocompatible polymer or resin or monomer injections could have at least one other opening or port in addition to the non-return valve opening in the access valve to enable the insertion of a light guide. These additional openings are micro-openings typically around ~1 mm in most cases but not exceeding 5 mm as required depending on the sleeve size (depending on the defect size), the number of light guides, and the diameter of the light guide. Because of the micro-sized openings and the laminated ends of the IM sleeve system (in the case of a multi-layered sleeve system), there exist numerous possibilities of inserting the light guide into the sleeve system to cure the photocurable polymer or resin or monomer that is injected into the IM sleeve. Some of the possibilities are schematically shown and explained in FIGS. 12A-12M.

In some embodiments, the light guide is first inserted into the sleeve system through the dedicated light guide opening in the access valve followed by the injection of the biocompatible polymer or resin, or monomer. In some embodiments, the optical light guide is inserted into the sleeve system through the dedicated light guide opening in the access valve that is self-closing and pressure-holding after the injection of the biocompatible polymer or resin, or monomer. In some embodiments, a light cable is assembled during the sleeve fabrication and is a part of the sleeve. In some embodiments, there can be multiple light guides of the same length and size or of different lengths and different sizes as a part of the sleeve system.

In some embodiments, light guides are inside the internal sleeve or uni-sleeve. In some embodiments, the light guide is in between the internal and external sleeve or outside the uni-sleeve. In some embodiments, the light guide is aligned with the sleeve direction. In some embodiments, the light guide is wrapped around the sleeve. In some embodiments, the light guide stays inside the sleeve after polymerization with the access valve opening sealed off. In some embodiments, the access valve allows the light guide to be removed and sealed off as required. The light guides have an overall diameter of about 1 mm to no more than 5 mm as required. The light guides are made with materials that are compatible with the injectable polymer. In some embodiments, the light guides are woven through the sleeves or affixed to the sleeve using biocompatible glues. In some embodiments, a light guide cable is the part of the woven fabric like individual fiber filaments that are used in braided, woven, or knitted fabrics.

Sleeve Customization and Continuous Monitoring: The advantage of using a multi-layered sleeve or using different sleeve materials and designs is the customization of the sleeve system for different bone defects, repair, and internal stabilization. The strength of the device depends on the sleeve system that is used for internal stabilization. For example, femur fractures that occur at the femoral neck, trochanteric, intertrochanteric, subtrochanteric, and shaft require high strength and load-bearing internal fixation. In such scenarios, a carbon fiber sleeve or any other high-strength sleeve that bonds to the injected polymer to extend the stiffness and strength becomes essential. In some embodiments, where load-bearing capacity is not essential, a uni-sleeve system made with implantable grade polymers will suffice.

As mentioned in previous sections, the concept of using a multi-layered customizable IM sleeve system would provide extremely beneficial and game-changer internal fixation for the pediatric population because even after internal fixation and post-implantation, the sleeve system would have the capability to expand and grow with the bone over and above the injected polymer. In geriatric populations, the sleeve system can be customized, and surface modified to carry bone morphogenetic proteins and drugs as required. The IM sleeve system can be fabricated with bioresorbable materials, demineralized bone matrix, coral-based bioactive materials, ceramics, etc.

Another important aspect of having an IM sleeve system is the provision of electronic sensors that can detect and convey the indicators such as pressure immediately after polymer injection, the temperature during curing, strain measurement during the process of healing following immediately after insertion and fixation, and temperature measurements during the process of cured polymer removal. In some embodiments, a MEMS-based pressure sensor with either capacitive or piezoresistive methods (to transform the membrane deflection into an electrical signal) is sewed or affixed onto the IM sleeve surface that is in apposition with the endosteum. In some embodiments, biocompatible glues will be used to affix the above-mentioned sensors without affecting their functioning of sensors.

Another important aspect of having an IM sleeve system is the provision of a surface modification of the IM sleeve to incorporate anti-bacterial drugs, proteins that enhance bone formation, and osseointegration of the IM sleeve with bone.

Removal Strategies: The advantage of having a multilayered IM sleeve system or a non-degradable sleeve system is that irrespective of whether the injected and cured polymer is removed, the removal of the implant becomes either minimally or less invasive. In certain situations, the implanted sleeve system remains in the patient for a lifetime. In some situations where removal of the sleeve system becomes necessary due to complications or where the device is no longer needed after complete healing, the sleeve system can be removed minimally invasively after the removal of the cured polymer by methods described in prior systems. Following the cured polymer removal, the IM sleeve removal will be achieved by using a micro flexible vacuum suction hose with or without additional attached tools at the end of the hose that is inserted inside the IM sleeve through the sleeve's access valve(s).

In some embodiments, the tip of the vacuum suction hose is inserted through the dedicated opening through the sealed access valve or through the only existing access valve located at either the proximal or distal side to apply sufficient vacuum and bring the internal sleeve near the valve. Once the internal sleeve collapses in the cavity and is disassociated with the external sleeve and endosteum, the sleeve is mechanically pulled through the access valve. In some embodiments where the applied vacuum is not sufficient or additional tools attached to the vacuum hose are not sufficient enough or for any other reason, a catheter system with an inflatable balloon similar to the one described in the insertion strategy will be used to mechanically lock the IM sleeve from the inside to enable its removal.

One of the possibilities of this removal is schematically shown in FIGS. 13A-13E. Briefly, after the removal of some or the entire cured polymer from the IM sleeve, the catheter is inserted into the IM sleeve through any possible opening from either the proximal or distal end access valve. The balloon(s) on the catheter is inflated to mechanically lock the sleeve interior and the IM sleeve is removed with the balloon(s) of the catheter remaining in the inflated position through the access valve or keyhole opening. In this scenario, the outer surface of the catheter balloon(s) can have a rough surface, special projections to lock the sleeve, or chemical coatings that would allow the bonding of the catheter to the IM sleeve interior. Since there could be a possibility of the residue of the cured polymer, the balloon(s) will be designed to engage, mechanically lock, and bond with the sleeve interior that has cured polymer residue.

Another strategy for removing the internal sleeve without the use of a vacuum or inflatable catheter could be by inserting a specialty sleeve retrieval cable through one of the access valves the retrieval cable contains appropriate provisions such as hooks, needle-like protrusions, etc, to enable latching and sleeve removal through the access valve. In some situations, the removal of the IM sleeve can be a step-by-step process where the internal sleeve is first retrieved, followed by the external sleeve. In some embodiments, the external sleeve no longer exists to be removed as it is made with bioresorbable materials, and the external sleeve is reabsorbed into the bone tissue. In some embodiments, the non-resorbable external sleeve is removed using any of the aforementioned strategies. In some embodiments, the external sleeve is removed by using a flexible intramedullary reamer that has vacuum suction inserted through the proximal or(and) distal key holes that were originally made for sleeve insertion. All the required tools for sleeve removal are contained in a sleeve removal kit that will be provided with the IM sleeve.

Pediatric fracture: Pediatric bone is skeletally immature, and bone fracture repair is unique and shows exceptional healing ability and may be treated by closed means with reduction and cast. However, an unstable open bone fracture requires surgical intervention and stabilization using implants. Conventionally, IM fixation in pediatric orthopedic fracture is done using Titanium Elastic Nails (TENS) or K-wires for forearm fracture and after 6 months to a year, they are surgically removed. This approach technically requires two invasive surgical interventions and may often lead to additional morbidity. The conventional pediatric IM rods are not designed to adapt to the physiological changes of the growing bone. The pediatric IM sleeve design is optimized to cater to the rapid linear growth and provide the necessary support for improved mineral apposition with the host bone, thereby preventing any future fracture risk that may happen post-implantation.

Young adult bone fracture: Young adult (18-35 years) bone fracture incidence is primarily due to overuse and stress fractures occurring during strenuous exercise, sports, injuries sustained during traumatic accidents, or during combat in military service members. Pediatric and young adult bone fractures could be attributed to underlying skeletal deficits, peak bone mass is a significant predictor of fracture risk and age-onset bone diseases. The Young Adult IM sleeve uses peak bone mass index to design sleeves with calcium phosphate reinforced materials or coated surfaces that are age-matched for improving the strength of the fractured bone and for osseointegration of the IM sleeve.

Middle Aged Adult bone fracture: Fracture risk incidence increases with age, and the Middle-Aged Adult IM sleeve is designed using bone mass index and age-matched fracture risk assessment methods that take into consideration the patient's age, sex, weight, height, previous fracture, and any diseases associated with BMD.

Geriatric fracture: Geriatric fractures are more common in the age group 65 and above. According to a 2004 Office of the Surgeon General report, roughly 1.5 million individuals suffer a fracture due to bone disease and 10 million individuals over age 50 in the US have osteoporosis of the hip, and an additional 33.6 million individuals over age 50 have low bone mass or osteopenia of the hip. Due to decreased bone density and increased brittleness, fracture fixation using the intramedullary nailing technique is often challenging. The Geriatric IM sleeve is structured to mimic the natural collagen orientation to provide the necessary biomechanical support and osseointegration. In another approach sleeves made with bioactive materials and demineralized bone are used that promote natural bone mineralization and osseointegration.

Pathological: Pathological bone fracture is due to a local or systemic pathological process. The Pathological IM sleeve, not only aids in the fracture fixation process, and the sleeve is customized to deliver drugs to treat the underlying bone pathologies.

The following are non-limiting examples of application of the presently claimed invention:

Pediatric fracture: A 8-year-old male patient with severe pain in the arm and a lack of mobility in his arm visits the hospital. A pediatric orthopedic surgeon performs an X-ray screening, and he identifies the oblique fracture in the proximal ulna. He highly recommends a minimally invasive fracture treatment using a pediatric sleeve (the present sleeve system with auxetic sleeve that expands and grows with bone) and a biocompatible polymeric resin system. In a minimally invasive fashion, the surgeon inserts the pediatric sleeve containing one access valve with two specialized openings, one to insert polymer and the other to insert polymer and sleeve removal accessories in the future. The surgical procedure is performed by injecting the biocompatible resin and curing it inside the sleeve and internally fixing the ulna. The patient is observed for a few hours before leaving the facility. The fracture heals and the boy completely recovers within 2 weeks. The surgeon performs a follow-up screening and recommends removing the IM device. Using the sleeve removal kit, the surgeon first removes the polymer and the sleeve using the removal catheter system. After the minimally invasive removal of the sleeve and device, the patient is discharged in a couple of hours.

Young adult bone fracture: 19-year-old female who fell on her arm on the slippery ice, comes to the hospital with extreme pain in her right arm. The physician performs an AP external rotation humerus X-ray and identifies the fracture in the surgical neck of the humerus. He refers him to the orthopedic surgeon and after watching the X-ray surgeon decide to use the minimally invasive fracture treatment using a three-dimensional sleeve system with three access valves suitable for neck fractures and an injectable polymer resin system. He performs surgery by bone reduction, creating three keyholes through the cortex, inserting the sleeve through one hole inside the medullary cavity of the humerus bone using two guides to set it in position until the sleeve can be accessed and visible by two other holes.

Confirming the sleeve position through radiographs, the guide wires are then removed which is followed by the injection of the polymer into the inserted sleeve and curing resin by using UV light. The patient shows a noticeable improvement in movement and recovers within 2 days. After a follow-up screening in a couple of months, the surgeon recommends removing the implant in a minimally invasive fashion using the access valves and three keyholes. The sleeve's openings in 3D sleeve three access valves are accessed through the three keyholes in the cortex to remove polymer using miniature ultrasonic tools followed by sleeve removal using a customized mechanical retriever. The entire process is performed in a minimally invasive fashion and the patient is discharged immediately. The patient doesn't feel any noticeable difference in his lifestyle.

Adult female phalanx fracture: A 35-year-old female comes with painful third digits of her left hand and she was not able to move her finger. The physician performs PA oblique X-ray and identifies it as a proximal phalanx fracture. He recommends the removable ultrathin unisleeve system with one access valve aligned longitudinally along the unisleeve length. The surgeon performs the surgery by inserting the unisleeve through the head of the proximal phalanx and positioning it in place inside the shaft and injecting an instant curable injectable polymer into the unisleeve using the access valve and fixing the fractured bone pieces together. The patient is discharged from the hospital after a few hours of observation, and she completely heals after two weeks. During the follow-up visit, the surgeon sets up another minimally invasive surgery to remove the implant. For removal, the surgeon first inserts the polymer removal accessory through the access valve, removes the polymer, and inserts a miniature mechanical retriever to remove the sleeve from the phalanx shaft. The incision is glued, and the patient walks out of the hospital with minimal to no inconvenience.

Pathological fracture: 85 years old male with severe osteoporosis falls down the stairs and is transported to the hospital as he was not able to move and was in excruciating pain. The emergency room (ER) specialist performed a mediolateral femur x-ray and identified a fracture in the midshaft of the femur. The orthopedic surgeon recommends fracture fixation using the high-strength bioactive sleeve system with one access valve containing two openings, one for injecting the high-strength photocurable resin and the second to insert the light guide. After bone reduction, the surgeon inserts the sleeve system inside the intramedullary cavity with the help of a guide wire and injects and cures the resin. The strong and tough IM device not only distributes the load and the drug-loaded and human recombinant bone morphogenetic protein-containing sleeve system will significantly fasten the fracture healing and help with patients' osteoporosis condition. The patient recovers in 4-6 weeks and because of no side effects and considering the complications with age, the surgeon preferred to leave the sleeves and IM device inside the cavity as it continued to help the patient with his physical activity.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An intramedullary sleeve apparatus (100) configured to hold and cure a curable material comprising injectable bone cement, curable resin, or a combination thereof to form an intramedullary device that conforms to a bone cavity of a bone and supports the bone during bone fracture treatment, the apparatus (100) comprising:
   a. an inner non-resorbable intramedullary sleeve (110), having at least one proximal end and at least one distal end, wherein an interior of the inner sleeve (110) comprises a reinforcing material (112);
   b. one or more access valves (130) disposed through the inner sleeve (110) so as to allow access into the inner sleeve (110), wherein each access valve is disposed at at least one proximal end of the inner sleeve (110), at least one distal end of the inner sleeve (110), or a combination thereof, wherein an access valve (130) of the one or more access valves comprises a first port (132) to allow for injection of the curable material, and a second port (134) to allow insertion of a light guide (140); and
   c. the light guide (140) disposed through the second port (134) of the access valve (130), the light guide (140) comprising a flexible plug (142) configured to seal the light guide (140) in the second port (134) of the access valve (130);
   wherein the apparatus (100) is configured to be removed by external accessories.

2. The apparatus (100) of claim 1, wherein a method for removing the apparatus (100) from the bone after removal of the curable material comprises:
   a. inserting a mechanically operated tool having a hook in a closed position through an access valve of the one or more access valves (130) until it reaches an end of the apparatus (100);
   b. releasing the hook and engaging the apparatus (100) through physical piercing; and
   c. pulling the tool out of the bone through the access valve, thereby removing the apparatus (100) from the bone.

3. The apparatus (100) of claim 1, wherein a method for removing the apparatus (100) from the bone after removal of the curable material comprises:
   a. inserting a vacuum hose through an access valve of the one or more access valves (130) until it reaches an end of the apparatus (100); and
   b. actuating the vacuum hose such that the apparatus (100) is sucked out of the bone through a laparoscopy hole.

4. The apparatus (100) of claim 1, wherein the inner sleeve (110) comprises a non-porous sleeve.

5. The apparatus (100) of claim 1 further comprising an outer intramedullary sleeve (120) disposed around the inner sleeve (110), having at least one proximal end and at least one distal end.

6. The apparatus (100) of claim 5, wherein the outer sleeve (120) comprises a porous sleeve or a non-porous sleeve.

7. The apparatus (100) of claim 5, wherein the outer sleeve (120) comprises an outer surface configured to be directly in contact with the bone cavity, wherein the outer surface of the outer sleeve (120) is surface modified for osseointegration with surrounding tissue, to have anti-microbial property, with load drugs, growth factors, peptides, and/or small molecules to induce bone growth in diseased bones, osteoporotic bones, and/or geriatric bones, or a combination thereof.

8. The apparatus (100) of claim 5 further comprising sensors built into an outer surface of the inner sleeve (110), an outer surface of the outer sleeve (120), or a combination thereof to quantify stress and motion between the inner sleeve (110) and the outer sleeve (120), the apparatus (100) and the bone.

9. The apparatus (100) of claim 1, wherein the inner sleeve (110) comprises an outer surface configured to be directly in contact with the bone cavity, wherein the outer surface of the inner sleeve (110) is surface modified for osseointegration with surrounding tissue, to have anti-microbial property, with load drugs, growth factors, peptides, and/or small molecules to induce bone growth in diseased bones, osteoporotic bones, and/or geriatric bones, or a combination thereof.

10. The apparatus (100) of claim 1 further comprising one or more fixation provisions at at least one proximal end and at least one distal end of the inner sleeve (110) for securing the apparatus (100) to the bone.

11. An orthopedic intramedullary sleeve apparatus (100) for internal bone fixation for fracture treatment of a bone of a patient, the apparatus (100) comprising a multilayer sleeve component comprising one or more access valves (130) disposed on a surface of the sleeve component, wherein each access valve comprises one or more resealable ports for injecting a curable material into the sleeve component, wherein an access valve of the one or more access valves comprises a first port to allow for injection of a curable material, and a second port to allow insertion of a light guide comprising a flexible plug configured to seal the light guide in the second port of the access valve.

12. The apparatus (100) of claim 11, wherein the sleeve component comprises an inner sleeve (110) and an outer sleeve (120).

13. The apparatus (100) of claim 12 further comprising one or more sensors disposed on an outer surface of the outer sleeve (120), the inner sleeve (110), or a combination thereof,
wherein each sensor of the one or more sensors is capable of measuring pressure, stress, strain, temperature, or a combination thereof with respect to the sleeve component and the bone.

14. The apparatus (100) of claim 12, wherein the inner sleeve (110) and the outer sleeve (120) are fabricated concurrently into a single sleeve with multi-functional features of the inner sleeve (110) and the outer sleeve (120) using electrospinning.

15. The apparatus (100) of claim 11, wherein the sleeve component is configured to conform to an intramedullary cavity of the bone and stretch to match growth of the bone.

16. A method for applying an intramedullary sleeve apparatus (100) to a fractured bone to bond to the bone during bone fracture treatment, the method comprising:
 a. providing the intramedullary sleeve comprising:
  i. an inner non-resorbable intramedullary sleeve (110), having at least one proximal end and at least one distal end;
  ii. an outer intramedullary sleeve (120) disposed around the inner sleeve (110), having at least one proximal end and at least one distal end;
   wherein the inner sleeve (110) and the outer sleeve (120) are bonded together; and
  iii. one or more access valves disposed through the inner sleeve (110) and the outer sleeve (120) so as to allow access into the inner sleeve (110), wherein each access valve is disposed at at least one proximal end of the inner sleeve (110) and the outer sleeve (120), at least one distal end of the inner sleeve (110) and the outer sleeve (120), or a combination thereof, wherein an access valve (130) of the one or more access valves comprises a first port (132) to allow for injection of a curable material, and a second port (134) to allow insertion of a light guide (140);
 b. creating one or more laparoscopy holes through a cortical layer of the bone at at least one distal end and at least one proximal end of the bone;
 c. applying one or more positioning guides to the intramedullary sleeve;
 d. positioning the one or more positioning guides between the one or more laparoscopy holes and through the bone;
 e. applying, by the one or more positioning guides, the intramedullary sleeve within the bone;
 f. injecting a curable material comprising injectable bone cement, curable resin, or a combination thereof through the first port (132) of the access valve (130);
 g. providing the light guide (140), the light guide (140) comprising a flexible plug (142);
 h. inserting the light guide (140) through the second port (134) of the access valve (130) such that the flexible plug (142) creates a seal that seals the light guide (140) in the second port (134) of the access valve (130); and
 i. actuating the light guide (140) such that the curable material is cured.

17. The method of claim 16, further comprising steps for removing the intramedullary sleeve from the bone after removal of the curable material, the steps comprising:
 a. inserting a mechanically operated tool having a hook in closed position through an access valve until it reaches an end of the sleeve;
 b. releasing the hook and engaging the sleeve through physical piercing; and
 c. pulling the tool out of the bone through the access valve (130).

18. The method of claim 16, wherein the inner sleeve (110) and the outer sleeve (120) are fabricated concurrently into a single sleeve with multi-functional features of inner and outer sleeve using electrospinning.

19. An intramedullary sleeve apparatus (100) configured to hold and cure a curable material comprising injectable bone cement, cured resin, or a combination thereof to form an intramedullary device that conforms to surrounding tissue and supports a bone of a patient during bone fracture treatment, the apparatus (100) comprising:
 a. an inner non-resorbable intramedullary sleeve (110), having at least one proximal end and at least one distal end, wherein an interior of the inner sleeve (110) comprises a reinforcing material (112);
b. an outer intramedullary sleeve (120) disposed around the inner sleeve (110), having at least one proximal end and at least one distal end;
c. one or more access valves (130) disposed through the inner sleeve (110) and the outer sleeve (120) so as to allow access into the inner sleeve (110), wherein each access valve is disposed at at least one proximal end of the inner sleeve (110) and the outer sleeve (120), at least one distal end of the inner sleeve (110) and the outer sleeve (120), or a combination thereof, wherein an access valve (130) of the one or more access valves comprises a first port (132) to allow for injection of a curable material, and a second port (134) to allow insertion of a light guide (140);
d. the light guide (140) disposed through the second port (134) of the access valve (130), the light guide (140) comprising a flexible plug (142) configured to seal the light guide (140) in the second port (134) of the access valve (130); and
e. one or more sensors disposed on an outer surface of the outer sleeve (120), the inner sleeve (110), or a combination thereof;
wherein each sensor of the one or more sensors is capable of measuring pressure, stress, strain, temperature, or a combination thereof with respect to the sleeve component and the bone;
wherein the inner sleeve (110) and the outer sleeve (120) are fabricated by electrospinning;
wherein the inner sleeve (110), the outer sleeve (120), or a combination thereof are configured to stretch to match growth of the bone;
wherein the apparatus (100) is configured to be removed by external accessories;
wherein one or more properties of the inner sleeve (110) and the outer sleeve (120) are determined based on a bone mass index of the patient;
wherein the inner sleeve (110) is configured to conform to the intramedullary cavity;
wherein the outer sleeve (120) is configured to conform to the intramedullary cavity and stretch to match growth of the bone.

20. The apparatus (100) of claim 19, wherein the reinforcing material (112) comprises carbon fiber, carbon fiber coated with thermoplastic resin, thermoset resin, or a combination resin, carbon nanotubes, graphite, polymer carbon fiber composite, glass fiber, polymer glass composite, cellulose, aramid, polymer ceramic composite, Polyether ether ketone (PEEK), dense Polytetrafluoroethylene (PTFE), expanded PTFE, Polyethylene terephthalate (PET), ultra-high-molecular-weight polyethylene (UHMWPE), titanium mesh, titanium-reinforced PTFE of a single material, polyether block amide, nylon, or a combination thereof.

21. The apparatus (100) of claim 19, wherein the inner sleeve (110) comprises one or more non-resorbable biocompatible materials comprising carbon fiber, polymer composites, non-resorbable materials such as dense polytetrafluoroethylene (PTFE), expanded PTFE, titanium mesh, and titanium-reinforced polytetrafluoroethylene of a single material, poly(acrylonitrile), poly(6-aminocaproic acid), poly(decamethylene adipamide), Nylon, Poly(etheretherketone) (PEEK), Poly(ethylene terephthalate) (PET), Polyurethane, PEBAX, poly(hexamethylene adipamide), poly(hexamethylene suberamide), poly(styrene), poly(4-methylpentene), high density polyethylene, ultra-high-molecular-weight polyethylene (UHMWPE), ethylene-vinyl acetate (EVA), modified EVA, polyvinylidene fluoride (PVDF), polyvinyl chloride (PVC), modified polyester of homopolymer or co-polymers, block copolymers, or a combination thereof.

22. The apparatus (100) of claim 19, wherein the outer sleeve (120) comprises one or more biocompatible materials comprising natural hydrogels, synthetic hydrogels, demineralized and decellularized bone, carbon fiber, polymer composites, bioceramics, bioactive glasses, glass-ceramics, polymer bioactive glass composites, poly(acrylonitrile), poly(6-aminocaproic acid), poly(decamethylene adipamide), Nylon 10,6, Poly(etheretherketone), PEEK, Poly(ethylene terephthalate), PET, poly(hexamethylene adipamide), Nylon 6,6, poly(hexamethylene suberamide), Nylon 6,8, poly(styrene), poly(4-methylpentene), high density polyethylene, ultra-high-molecular-weight polyethylene, polytetrafluoroethylene PTFE, expanded PTFE, modified ethylene-vinyl acetate, modified polyester of homopolymer or co-polymers, block copolymers, or a combination thereof.

23. The apparatus (100) of claim 19, wherein the flexible plug (142) comprises natural rubber, styrene butadiene rubber, butyl rubber, nitrile, neoprene, ethylene propylene diene monomer based rubber, silicone, fluoroelastomer (FKM), polyurethane based rubber, hydrogenated nitrile rubber, or a combination thereof.

24. The apparatus (100) of claim 19, wherein the one or more access valves (130) comprise silicone, silicone-based materials, synthetic or natural based elastomeric rubber materials including natural rubber, styrene butadiene rubber, butyl rubber, nitrile, neoprene, ethylene propylene diene monomer based rubber, silicone, fluoroelastomer (FKM), polyurethane based rubber, hydrogenated nitrile rubber, or a combination thereof.

* * * * *